(12) United States Patent
Hathaway

(10) Patent No.: US 7,402,407 B1
(45) Date of Patent: Jul. 22, 2008

(54) CHEMICALLY TARGETED POSITIONAL IDENTIFICATION OF POST-TRANSLATIONALLY PHOSPHORYLATED PEPTIDES

(75) Inventor: Gary M. Hathaway, Sierra Madre, CA (US)

(73) Assignee: California Institute of Technology, Pasadena, CA (US)

( * ) Notice: Subject to any disclaimer, the term of this patent is extended or adjusted under 35 U.S.C. 154(b) by 330 days.

(21) Appl. No.: 10/938,371

(22) Filed: Sep. 10, 2004

Related U.S. Application Data

(60) Provisional application No. 60/508,422, filed on Oct. 3, 2003.

(51) Int. Cl.
*C12Q 1/37* (2006.01)
*C12P 21/06* (2006.01)
*C07K 1/107* (2006.01)

(52) U.S. Cl. .......................... 435/24; 435/23; 435/69.7; 530/402; 530/412; 530/413; 930/20

(58) Field of Classification Search ....................... None
See application file for complete search history.

(56) References Cited

OTHER PUBLICATIONS

Jeno et al., Interna Sequences from proteins digesed in polyacrylamide gels. Anal. Chem., 224, 75-82, 1995.*
Morpugo et al., N-hydroxysuccinimide carbonates and carbamates are useful reactive reagents for coupling ligands to lysines on proteins., J. Biochem. Byophys methods, 38, 17-28, 1999.*
Carr et al., "Selective Detection and Sequencing of Phosphopeptides at the Femtomole Level by Mass Spectrometry," *Analytical Biochemistry*, vol. 239: pp. 180-192 (1996).
Catsimpoolas and Wood, "Specific Cleavage of Cystine Peptides by Cyanide," *The Journal of Biological Chemistry*, vol. 241, No. 8: pp. 1790-1796 (1966).
Cole, David, "S-Aminoethylation," *Methods in Enzymology*, vol. 11: pp. 315-317 (1967).
Gerken et al., "Determination of the Site-specific O-Glycosylation Pattern of the Porcine Submaxillary Mucin Tandem Repeat Glycopeptide," *The Journal of Biological Chemistry*, vol. 272, No. 15: pp. 9709-9719 (1997).
Greis et al., "Selective Detection and Site-Analysis of O-GlcNAc-Modified Glycopeptides by β-Elimination and Tandem Electrospray Mass Spectrometry," *Analytical Biochemistry*, vol. 234: pp. 38-49 (1996).

Havlis et al. "Fast-Response Proteomics by Accelerated In-Gel Digestion of Proteins," *Anal. Chem.* vol. 75: pp. 1300-1306 (2003).
Helmbrecht et al., "Chaperones in cell cycle regulation and mitogenic signal transduction: a review," *Cell Prolif.* vol. 33:pp. 341-365 (2000).
Huang et al., "Matrix-assisted laser desorption/ionization mass spectrometry compatible β-elimination of O-linked oligosaccharides," *Rapid Communications in Mass Spectrometry*, vol. 16: pp. 1199-1204 (2002).
Hunziker et al., "Peptide Fragmentation Suitable for Solid-Phase Microsequencing," *Biochem. J.*, vol. 187: pp. 515-519 (1980).
Kawata et al., "Amino-acid sequence of ribonuclease $T_2$ from *Aspergillus oryzae*," *Eur. J. Biochem.*, vol. 176: pp. 683-697 (1988).
Masaki et al., "Hydrolysis of S-2 Aminoethylcysteinyl Peptide Bond by *Achromobacter* Protease I," *Biosci. Biotech. Biochem.*, vol. 58, No. 1: pp. 215-216 (1994).
Meyer et al., "Sequence analysis of phosphoserine-containing peptides," *FEBS Letters*, vol. 204, No. 1: pp. 61-66 (1986).
Rademaker et al., "Mass Spectrometric Determination of the Sites of O-Glycan Attachment with Low Picomolar Sensitivity," *Analytical Biochemistry*, vol. 257: pp. 149-160 (1998).
Rall et al., "The Amino Acid Sequence of Ferredoxin from *Clostridium acidi-urici*," *Biochemistry*, vol. 8, No. 6: pp. 2486-2496 (1969).
Rusnak et al., "Identification of Phosphorylated and Glycosylated Sites in Peptides by Chemically Targeted Proteolysis," *Journal of Biomolecular Techniques*, vol. 13, No. 4: pp. 228-237 (2002).
Schwartz et al., "*N*-(β-Iodoethyl)trifluoroacetamide: A New Reagent for the Aminoethylation of Thiol Groups in Proteins," *Analytical Biochemistry*, vol. 106: pp. 43-48 (1980).
Steen and Mann, "A New Derivazation Strategy for the Analysis of Phosphopeptides by Precursor Ion Scanning in Positive Ion Mode," *J. Am. Soc. Mass Sepctrom.* vol. 13: pp. 996-1003 (2002).
Thompson et al., "Characterization of Protein Phosphorylation by Mass Spectrometry Using Immobilized Metal Ion Affinity Chromatography with On-Resin β-Elimination and Michael Addition," *Anal. Chem.*, vol. 75: pp. 3232-3243 (2003).
Tomita and Marchesi, "Amino-acid sequence oligosaccharide attachment sites of human erythrocyte glycophorin," *Proc. Nat. Acad. Sci. USA*, vol. 72, No. 8: pp. 2964-2968 (1975).

* cited by examiner

*Primary Examiner*—Lorraine Spector
*Assistant Examiner*—Elly-Gerald Stoica
(74) *Attorney, Agent, or Firm*—DLA Piper US LLP

(57) ABSTRACT

Methods are provided for determining the position of a post-translationally modified (PTM) amino acid residue such as a phosphorylated amino acid residue or an O-glycosylated amino acid residue in a peptide. Also provided are methods for determining the identity of a PTM amino acid residue in a peptide. In addition, kits for practicing such methods are provided.

27 Claims, 5 Drawing Sheets

US 7,402,407 B1

CHEMICALLY TARGETED POSITIONAL IDENTIFICATION OF POST-TRANSLATIONALLY PHOSPHORYLATED PEPTIDES

CROSS REFERENCE TO RELATED APPLICATION(S)

This application claims the benefit of priority under 35 U.S.C. § 119(e) of U.S. Ser. No. 60/508,422, filed Oct. 3, 2003, the entire content of which is incorporated herein by reference.

BACKGROUND OF THE INVENTION

1. Field of the Invention

The invention relates generally to methods for characterizing proteins and more specifically to methods and compositions for chemically modifying a peptide such that phosphorylated and/or glycosylated amino acid residues can be identified by enzymatic or chemical cleavage at the peptide bond adjacent to the modified residue.

2. Background Information

The emergence of proteomics is allowing characterization of protein expression in various cells and cell types, and the identification of differences in protein expression that are associated with cell pathologies. As such, proteomics holds the promise of providing diagnostic methods based on patterns of protein expression characteristic of the particular state of a population of cells. For example, the identification of specific protein expression in cells can provide valuable information where a mutation results in the loss of expression of a protein, and the loss of expression correlates with a particular disease.

Such an approach for analyzing cells is limited, however, in that protein expression is not a static event. Instead, protein expression can increase or decrease in response to physical, chemical, biological, or environmental conditions, as well as at various times, including, for example, during development and/or during the cell cycle. Further, a protein may be modified following expression due, for example, to a proteolytic event that converts an inactive zymogen to an active polypeptide or to modification of one or more amino acids that regulates the activity of the polypeptide. Thus, an examination that is limited to the simple identification of the presence or absence of one or more proteins, or even to the level of expression of proteins, provides, at best, a starting point for proteome analysis.

Cellular regulatory mechanisms involving post-translational modification (PTM) of proteins are an integral part of any description of protein dynamics characteristic of the cellular state (proteome). Phosphorylation, for example, generally is a transient PTM that can dictate whether a protein is active or inactive. The importance of phosphorylation is indicated by the expression of more than one hundred protein kinases, and as many protein phosphatases, in vertebrates cells. Historically, reversible PTMs such as phosphorylation and glycosylation have been difficult to characterize.[1-8] Initially, radiochemical labeling was used to identify phosphopeptides and glycopeptides derived from enzymatic or chemical digests of proteins.[8,9] However, the method was time-consuming, tedious, and suited only to relatively short phosphopeptides, and even then, the data provided only positional information for the radiolabel obtained.

Direct, automated sequencing of phosphopeptides was made possible with the introduction of a chemistry that converted the phosphoamino acid to a form detectable in gas phase sequencing[10]. While peptides glycosylated on serine and threonine reportedly gave no signal during Edman degradation, their monoglycosylated residues could be detected as their phenylthiohydantoin (PTH) derivatives.[11-13] Unfortunately, these derivatives co-eluted with serine, glutamine, and glycine peaks, making unambiguous assignment difficult. Although direct N-terminal sequencing provides quantitative and complete sequence information, sequencing must start from an N-terminus specified by the method of cleavage, which may be distant from the site of modification.

To a considerable extent, the above described difficulties have resulted in mass spectrometry (MS) supplanting chemical sequencing.[11,14-16] Unfortunately, MS suffers certain various drawbacks, including, for example, that it generally is not quantitative, though it can be made so with difficulty.[17] Also, tandem MS of phosphopeptides and glycopeptides following collisional activation tends to give primarily the parent peptides or requires extensive manipulatory methods and intensive inspection of MS spectra.[5,15,18-20] Furthermore, phosphopeptides tend to ionize poorly, particularly in positive ion mode, and upon collisional activation yield fewer peptide fragments than non-phosphopeptides. A major drawback of tandem mass analysis is that large peptides tend to give incomplete or no sequence information upon low energy collision.[21,22] Thus, a need exists for methods that allow the identification of post-translationally modified amino acid residues such as phosphoamino acids in peptides.

SUMMARY OF THE INVENTION

The present invention is based on the development of methods and compositions for the chemically targeted identification (CTID™) method of post-translationally modified (PTM) amino acid residues. The CTID™ method of PTM amino acid residues is exemplified with respect to phosphorylated and glycosylated residues in peptides, wherein phosphoserine, phosphothreonine, O-glycosylserine, and O-glycosylthreonine were chemically modified to protease-sensitive 2-aminoethylcysteine and/or β-methyl-aminoethylcysteine derivatives (lysine analogs) by β-elimination and Michael addition reactions. Following cleavage of the peptides at the positions of the resultant lysine analogs with *Achromobacter* lysyl endopeptidase, the cleavage products were analyzed by mass spectrometry and by N-terminal Edman degradation. When acetylation was carried out as a first step, direct N-terminal chemical sequencing of the digests yielded sequences immediately C-terminal to the phosphorylated or glycosylated residues. Assignment of the positions of the PTM amino acid residues was obtained from the chemical sequence data and from the mass data. Accordingly, the present invention provides compositions and methods for identifying and characterizing phosphorylated and/or glycosylated residues in peptides, including for rapidly sequencing large, multiply phosphorylated and/or glycosylated peptides derived from post-translationally modified proteins, for example, by mass spectrometry and/or Edman chemical degradation.

The present invention relates to a method for chemically targeted identification of a position of at least one post-translationally modified (PTM) amino acid residue in at least one peptide. A CTID™ method of the invention can be performed, for example, by treating a sample that includes at least one peptide (e.g., 1, 2, 3, 4, 5, 6, or more peptides) with at least one reagent that can chemically modify a PTM amino acid residue of a peptide, whereby, when a peptide includes at least one PTM amino acid residue, the PTM amino acid residue is chemically modified to generate a peptide containing at least one chemically modified amino acid residue; and contacting the peptide containing the chemically modified amino acid residue(s) with the proteolytic agent (e.g., an enzyme or a chemical agent), whereby the peptide is cleaved at the position of the chemically modified amino acid residue(s) to produce cleavage products indicative of the position of a PTM amino acid(s) residue in the peptide, thereby identifying the position of at least one PTM amino acid residue in at least one peptide. According to the present methods, a peptide containing a chemically modified amino acid residue is susceptible to cleavage by a proteolytic agent at a position of a chemically modified amino acid residue, whereas the peptide is not susceptible to cleavage by the proteolytic agent at the position of the PTM amino acid residue prior to chemically modifying the PTM amino acid residue.

A PTM amino acid residue, the position of which can be identified according to the present methods, can be an amino acid residue having any type of post-translational modification, including a post-translational modification that occurs naturally in a prokaryotic cell or a eukaryotic cell (e.g., a plant cell, and/or a mammalian cell) or that can be effected on an amino acid residue of a peptide using a chemical method. As such, the post-translational modification can include, for example, phosphorylation, acetylation, farnesylation, and glycosylation.

In one embodiment, the CTID™ method is practiced with respect to a phosphorylated amino acid residue. In one aspect of this embodiment, the PTM amino acid residue is phosphoserine and/or phosphothreonine. In another embodiment, the CTID™ method is practiced with respect to a glycosylated amino acid residue. In one aspect of this embodiment, the amino acid residue is an O-glycosylated amino acid residue, particularly O-glycosylserine and/or O-glycosylthreonine. The CTID™ method of the invention can be performed with respect to phosphorylated and/or O-glycosylated serine and/or threonine residues, for example, by treating the sample containing the peptide(s) with a first reagent, which includes a base that can effect β-elimination of the PTM amino acid residue of the peptide to generate an alanine derivative (e.g., dehydroalanine, β-methyl-dehydroalanine or aminoalanine), and a second reagent, which includes a nucleophile that can effect Michael addition to the alanine derivative, thereby generating a chemically modified amino acid residue comprising a lysine analog.

A first reagent useful in the present methods can include, for example, sodium hydroxide and/or barium hydroxide, which can effect β-elimination of a phosphate group from phosphoserine or phosphothreonine to generate dehydroalanine or β-methyl-dehydroalanine, respectively, or can include ammonium hydroxide, which can effect β-elimination of an O-glycosyl group from O-glycosylserine or O-glycosylthreonine to generate aminoalanine or β-methyl-aminoalanine, respectively (see, e.g., Rademaker et al., *Anal. Biochem.* 257: 149-160, 1998, which is incorporated herein by reference). A first reagent for chemically modifying an O-glycosylated serine or threonine residue also can include a borane-ammonia complex in aqueous ammonia, wherein a modified β-elimination occurs. A first reagent containing borane-ammonia complex in aqueous ammonia provides the additional advantage that the glycosyl group is released in an intact form and, therefore, can be characterized, if desired, (e.g., using mass spectrometry). A second reagent useful in the present methods can be any reagent that effects a Michael addition, including, for example, 2-aminoethanethiol (2-AET; cysteamine), 1,2-diaminoethane (1,2-DAE; ethylenediamine), or thiocyanic acid.

A proteolytic agent useful in the present methods include any agent that specifically cleaves a peptide at the position (i.e., the peptide bond immediately N-terminal or C-terminal) of the chemically modified PTM amino acid residue, but not at the position of the PTM amino acid residue prior to its being chemically modified. For example, the proteolytic agent can be a chemical reagent or an enzyme. In one embodiment, the proteolytic agent is an endopeptidase that cleaves the peptide at the position of the chemically modified amino acid residue(s). For example, where the PTM amino acid residue is a serine or threonine residue that is chemically modified by β-elimination and Michael addition to generate a lysine analog, the endopeptidase can be a lysine endopeptidase such as *Achromobacter lyticus* lysyl endopeptidase ("lysyl endopeptidase") or *Lysobacter enzymogenes* endoprotease Lys-C ("Lys-C"), each of which can specifically cleave a peptide C-terminal to the lysine analog to generate a cleavage product containing the chemically modified amino acid residue (lysine analog) at its C-terminus.

A CTID™ method of the invention can be performed in any of a variety of ways. For example, where at least one peptide of a sample contains one or more of a phosphoserine residue and/or a phosphothreonine residue, the sample can be treated using a first reagent containing barium hydroxide, alone, or in combination with sodium hydroxide, and a second reagent containing 2-AET, and the peptide containing the chemically modified amino acid residue(s) can be contacted with lysyl endopeptidase. Alternatively, or in addition, where at least one peptide of the sample contains one or more of a phosphoserine residue and/or a phosphothreonine residue, the sample can be contacted with a first reagent that contains sodium hydroxide and barium hydroxide, and a second reagent that contains 1,2-DAE, and the peptide containing the chemically modified amino acid residue(s) can be contacted with Lys-C. In another example, where at least one peptide of the sample contains one or more of an O-glycosylserine residue and/or an O-glycosylthreonine residue, the sample can be contacted with a first reagent containing ammonium hydroxide (or borane-ammonia complex in aqueous ammonia), and a second reagent containing 2-AET (or 1,2-DAE), and the peptide containing the chemically modified amino acid residue(s) can be contacted with lysyl endopeptidase (or Lys-C). In one aspect, the CTID method is performed in whole or in part using peptides bound in solid state to reverse phase media. In another aspect, the CTID method relates to the quantitative measurement of post-translational modification by use of heavy isotopes of the nucleophile such that, by comparing the signals obtained by mass spectrometry for samples modified with the heavy isotope with those from samples modified with light isotopes, a relative quantitation can be obtained. Isotopic substitution of the nucleophile can utilize, for example, heavy isotopes of hydrogen, carbon, nitrogen and sulfur.

The CTID™ method of identifying the position of a PTM amino acid residue can further include blocking one or more substrate amino acid residues in the peptide. The substrate amino acid residue can be any amino acid residue that is not a PTM amino acid residue to be chemically modified according to the present methods, but that otherwise is susceptible to being chemically modified by the first and/or second reagent, and/or that can act as a cleavage site for a proteolytic agent to be used in the method. Where a peptide to be examined contains an amino acid residue susceptible to being chemically modified by a first and/or second reagent, blocking of the substrate amino acid residue is performed prior to contacting the sample with the reagent. For example, where the method utilizes a second reagent containing 2-AET, and the peptide contains cysteine, which can be chemically modified by 2-AET, the cysteine residue(s) can be blocked prior to treating the sample with 2-AET. Where the peptide contains an amino acid residue susceptible to cleavage by a proteolytic agent to be used, blocking of the substrate amino acid residue is performed prior to contacting the peptide with the proteolytic agent. For example, where the CTID™ method utilizes lysyl endopeptidase as the proteolytic agent, and the peptide contains lysine, which can act as a substrate for cleavage by lysyl endopeptidase, the lysine residue(s) can be blocked prior to contacting the peptide with the lysyl endopeptidase (e.g., prior to treating the sample with the first and/or second reagent).

The position of a PTM amino acid residue can be identified by examining one or more cleavage products generated following contact with the proteolytic agent. Identification of a PTM amino acid residue can be determined by sequencing all or a portion of one or more cleavage products, which generally contain the PTM amino acid residue at a C-terminus or N-terminus. Where the amino acid sequence of the peptide is known, the PTM amino acid residue can be identified by determining the mass of one or more of the cleavage products, wherein the mass is indicative of the position of the PTM amino acid residue, or by determining the amino acid residue present at a terminus formed pursuant to the cleavage. For example, where a peptide having a known sequence, including two serine residues, one of which is phosphorylated, is examined by treating the peptide with base and 2-AET, and contacting the peptide containing the chemically modified amino acid residue with lysyl endopeptidase, two cleavage products are generated, including an N-terminal fragment containing the PTM amino acid residue at its C-terminus and a C-terminal fragment. In this example, the position of the PTM amino acid residue can be determined, for example, by determining the mass of one or both cleavage products (e.g., using mass spectrometry), wherein the mass is indicative of the cleavage position and, therefore, the PTM amino acid position. Alternatively, or in addition, the N-terminal amino acid residue of the C-terminal fragment can be determined (e.g., using the Edman reaction), thus indicating the position of the cleavage and, therefore, the position of the PTM amino acid residue (i.e., the residue immediately N-terminal (in the intact peptide) to the N-terminal amino acid residue of the C-terminal fragment). As such, a method of identifying the position of a PTM amino acid residue in a peptide can further include determining the identity of the PTM amino acid residue.

A sample that is examined according to the present methods can contain a single peptide or can contain a plurality (e.g., 2, 3, 4, 5, or more) of peptides, which can be same peptides having different types of post-translational modifications, different peptides having the same type of post-translational modifications, different peptides having different types of post-translational modifications, or any combinations of such peptides, some or all of which can contain one or more PTM amino acid residue(s). In one embodiment, a plurality of peptides includes peptide fragments of a protein that contains or is suspected of containing at least one PTM amino acid residue. In another embodiment, one or more peptide fragments of a protein is/are isolated prior to practicing the present methods. Peptide fragments of a protein (e.g., a glycoprotein or a phosphoprotein) can be obtained using chemical or enzymatic methods.

Where the CTID™ method is practiced, for example, using a first reagent containing sodium hydroxide, a second reagent containing 2-AET, and lysyl endopeptidase, the position of a phosphorylated and/or O-glycosylated amino acid residue can be identified. Absent additional information, however, it may not be possible to determine the type of post-translational modification (i.e., phosphorylation or O-glycosylation). Accordingly, the method can further include identifying the particular type of post-translational modification. Such a method, which can be practiced in parallel or serially with the CTID™ method of identifying the position of a PTM amino acid residue, can be performed in a second reaction using an aliquot of the sample containing the peptide(s). The aliquot is substantially identical to the sample and/or peptide(s) being examined and generally, but not necessarily, is a portion of the same sample containing the peptide(s) for which the PTM amino acid residue position(s) is being identified.

In one embodiment, the method of determining the type of post-translational modification allows a determination to be made as to whether a PTM amino acid residue comprises a phosphoamino acid or an O-glycosylated amino acid residue. In one aspect, the method is performed by obtaining an aliquot of the sample (or otherwise substantially identical sample), prior to chemically modifying the PTM amino acid residue, contacting the aliquot with a glycosidase, then treating the aliquot with the reagent that can chemically modify the PTM amino acid residue, when present, and contacting the aliquot with the proteolytic agent. Upon performing such a method, cleavage of the peptide of the aliquot will be the same as or different from cleavage of the peptide that was not treated with the glycosidase. Where cleavage of the peptide of the aliquot (i.e., treated with the glycosidase) corresponds to cleavage of the peptide not treated with the glycosidase, a determination is made that the PTM amino acid residue is a phosphoamino acid residue (i.e., the glycosidase had no effect on the PTM amino acid residue). In comparison, where no cleavage of the peptide of the aliquot occurs, and the peptide not treated with the glycosidase is cleaved, a determination is made that the PTM amino acid residue comprising an O-glycosylated acid residue (i.e., the glycosidase removed the glycosyl group from the PTM amino acid residue, thus preventing chemical modification of the residue).

In another aspect, the method is performed by obtaining an aliquot of the sample, prior to chemically modifying the PTM amino acid residue, contacting the aliquot with a phosphatase, then treating the aliquot with the reagent that can chemically modify the PTM amino acid residue, when present, and contacting the aliquot with the proteolytic agent. Upon performing such a method, cleavage of the peptide of the aliquot will be the same as or different from cleavage of the peptide that was not treated with the phosphatase. Where cleavage of the peptide of the aliquot (i.e., treated with the phosphatase) corresponds to cleavage of the peptide not treated with the phosphatase, a determination is made that the PTM amino acid residue is an O-glycosylated amino acid residue. In comparison, where no cleavage of the peptide of the aliquot occurs, and the peptide not treated with the glycosidase is cleaved, a determination is made that the PTM amino acid residue comprising a phosphoamino acid residue.

The present invention also relates to a method for identifying a position of at least one phosphoserine, phosphothreonine, O-glycosylserine, or O-glycosylthreonine PTM amino acid residue in at least one peptide. Such a method can be performed, for example, by chemically modifying the PTM amino acid residue of at least one peptide of a sample to produce a lysine analog, thereby generating a peptide containing at least one lysine analog; and contacting the peptide containing the lysine analog with a lysine specific proteolytic agent, whereby the peptide is cleaved at the position of the lysine analog to produce cleavage products indicative of the position of a PTM amino acid residue in the peptide. In one embodiment, the step of chemically modifying the PTM amino acid residue of the peptide is performed by contacting the phosphoserine, phosphothreonine, O-glycosylserine, and/or O-glycosylthreonine residue(s) with a first reagent, which includes a base that effects β-elimination of the PTM amino acid residue to generate an alanine derivative, and a second reagent, which includes a nucleophile that effects Michael addition of the alanine derivative. In one aspect of this embodiment, the nucleophile of the second reagent is 2-AET. In another embodiment, the lysine specific proteolytic agent is an enzyme (e.g., lysyl endopeptidase or Lys-C).

In practicing the present CTID™ methods, the peptide containing the PTM amino acid residue can be coupled to a solid support. The solid support can be any solid material to which a peptide can be coupled directly (e.g., via a terminal amino or carboxy group) or indirectly (e.g., via a linker molecule), and that is stable to the conditions under which the method steps are performed (e.g., stable to basic conditions). For example, the solid support can be a bead; a glass slide; a well, or a chip. Because only a peptide containing a PTM amino acid residue is cleaved by a proteolytic agent according to the present methods, an advantage of coupling peptides to be examined to a solid support is that peptides that do not contain a PTM amino acid residue remain bound to the support, whereas cleavage products of peptides containing a PTM amino acid residue are released from the support, thus facilitating detection of the cleavage products.

The CTID™ methods of the invention can be performed in any of various formats, including, for example, as a single assay of a single peptide (i.e., a homogenous population of the same peptide); or in a multiplex format, wherein a plurality of peptides is examined in a single sample. The use of mass spectrometry to analyze cleavage products can be particularly useful for performing a multiplex analysis because mass spectrometry can readily detect small molecular mass differences between peptides/cleavage products of a mixed population and, therefore, can detect several different peptides/cleavage products in a single run.

The CTID™ methods also conveniently can be adapted to and performed in a high throughput format, wherein a plurality of samples, some or all of which can contain one peptide or a plurality of peptides, can be examined in parallel. High throughput assays provide the advantage that numerous samples can be examined in parallel, thus allowing, for example, for the inclusion of appropriate controls, or for the examination of several different samples under substantially identical conditions, or for the examination of several same samples under different conditions. Further, high throughput assays are readily adaptable to automation, thus reducing costs, as well as reducing the potential for random errors. A high throughput assay can be performed, for example, in wells of a plate, or in delineated regions of a chip or glass slide. For example, a solid support such as a silicon based chip or glass slide can be modified to contain pits, into which a sample can be deposited, or to contain functional linker molecules, wherein samples containing peptides to be examined can be deposited in specified positions under conditions such that the peptides are coupled to the support. In one embodiment, the samples are deposited in a defined pattern such as array, which can be an addressable array. An addressable array can facilitate identification of particular samples, as well as automation of the steps for performing the method.

The present invention also relates to a kit, which contains components useful for practicing a CTID™ method of identifying a position of a PTM amino acid residue in a peptide. Such a kit can contain, for example, a reagent that effects β-elimination of a phosphoserine, phosphothreonine, O-glycosylserine, or O-glycosylthreonine residue of a peptide to produce an amino acid analog Michael acceptor; a reagent that includes a nucleophile that can interact with the amino acid Michael acceptor to produce a chemically modified amino acid residue in a peptide; and a proteolytic agent that can cleave a peptide at a position of a chemically modified amino acid residue formed by β-elimination and Michael addition of the chemically modified residue. In one embodiment, the kit contains two or more reagents that effect β-elimination, and/or two or more nucleophile that can interact with the amino acid Michael acceptor; and/or two or more proteolytic agents, such a kit allowing the user an option of selecting one or more components for a particular assay.

A kit of the invention also can contain one or more other component(s) that can be useful for practicing the present methods and/or analyzing the results. For example, the kit can contain a component that can be useful as a control, or for standardizing an assay, (e.g., a peptide that contains at least one phosphoamino acid residue). The kit also can contain, for example, one or more glycosidases, one or more phosphatases, or a combination of glycosidase(s) and phosphatase(s).

DETAILED DESCRIPTION OF THE INVENTION

Figure 1:
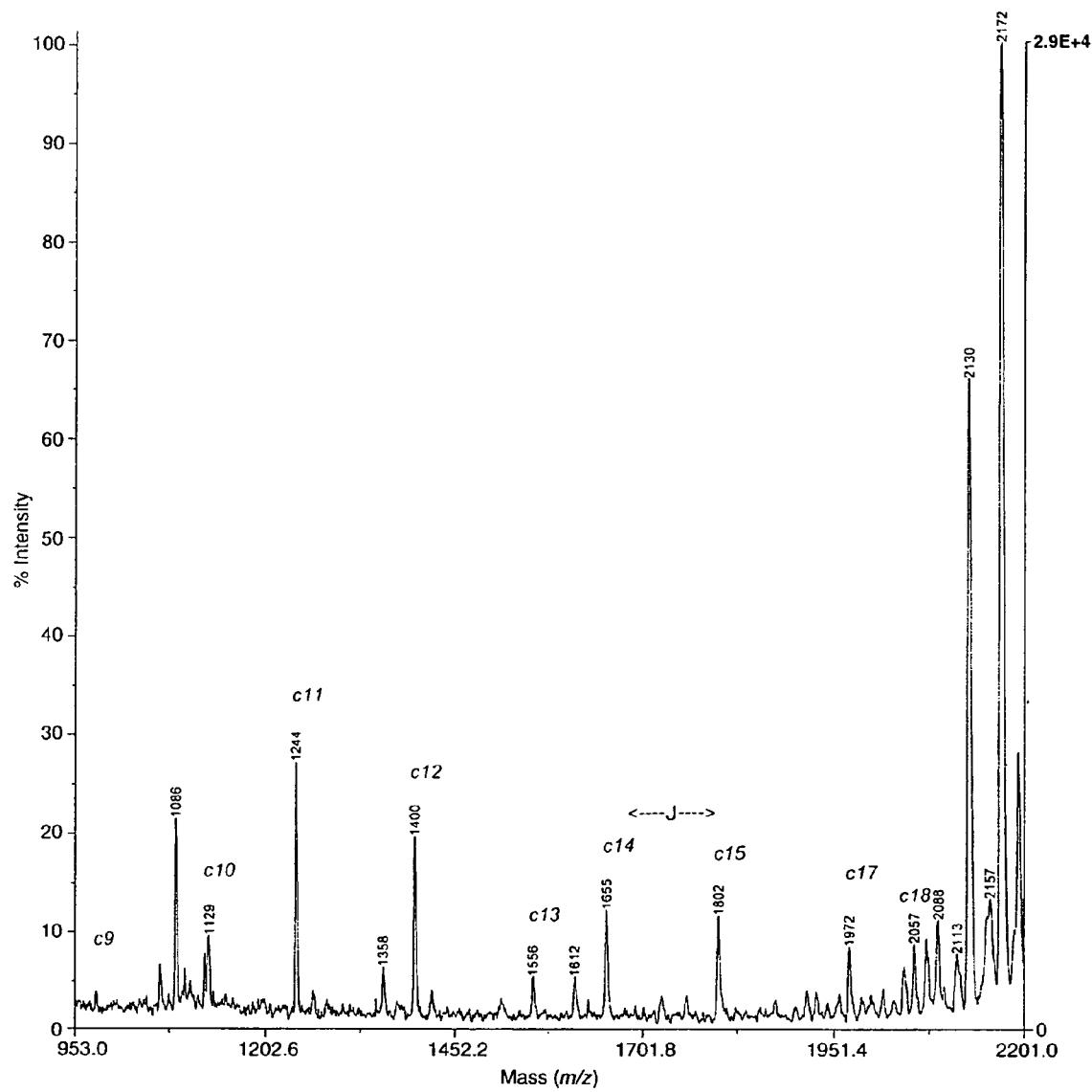
FIG. 1 shows a MALDI-TOF in-source decay sequence analysis of the 2-aminoethylcysteine derivative of the CNS peptide (SEQ ID NO:3). The sequence of the unacetylated peptide could be read from the nearly complete C ion series. The mass difference between the C14 and C15 ions (labeled "J") corresponds to the 2-aminoethylcysteine.

The present invention is based on the discovery that the positions of post-translationally modified (PTM) amino acid residues, including phosphorylated amino acid residues and O-glycosylated amino acid residues, in a peptide can be identified by chemically modifying the PTM amino acid residue such that the position of the peptide containing the chemically modified amino acid residue becomes susceptible to proteolytic cleavage. Chemical modification of the PTM amino acid residue(s) followed by proteolytic cleavage yielded smaller peptides that were easily sequenced by collision activated dissociation with product ion analysis (see Example 1; see, also, Rusnak et al., *J. Biomol. Tech.* 13:228, 2002, which is incorporated herein by reference). Amino-terminal sequencing provided both positional and quantitative information. When the chemically modified residue was oxidized to its sulfenic acid, neutral (93) loss was observed (Steen and Mann, *J. Amer. Soc. Mass Spectrom.* 13:996-1003, 2002, which is incorporated herein by reference), and also a precursor ion (94[+]) was also observed.

As disclosed herein, methods for chemical sequencing and/or mass analysis of large phosphopeptides and O-glycosyl peptides have been developed. The chemically targeted identification (CTID™) methods of the invention facilitate the study of large phosphopeptides and glycopeptides by providing a means to determine the specific position of PTM amino acid residues. Further, when combined with the availability of extensive protein databases, which can be used to formulate, guide and interpret experimental results, the present methods conveniently allow the identification of a phosphoamino acid residue(s) and O-glycosylated amino acid residue(s) in a PTM protein. Using the present methods, peptide masses or a few residues of sequence on either side of a target site can provide sufficient information such that the modified residue and, in many cases, the extent of the modification can be specified.

Accordingly, the present invention provides methods for identifying the position of one or more PTM amino acid residue in a peptide. As used herein, the term "position", when used in reference to a PTM amino acid of a peptide, means the location of the PTM amino acid in the primary amino acid sequence of the peptide. For example, the PTM amino acid residue (phosphothreonine) is peptide PS (SEQ ID NO:1; see Table 1, below; SEQ ID NOS:1-4) is at position 5 of the heptapeptide. According to the present methods, a PTM amino acid residue is converted to a chemically modified amino acid residue, wherein a proteolytic agent can cleave the peptide at the position of the chemically modified amino acid residue. Reference herein to "cleaving a peptide at a position of a chemically modified amino acid residue" means that the proteolytic agent cleaves the peptide bond that is immediately N-terminal or immediately C-terminal to the chemically modified residue. For example, with reference to peptide PS (SEQ ID NO:1), wherein the phosphothreonine is chemically modified to generate the lysine analog, 2-amionethylcysteine, and the peptide is contacted with lysyl endopeptidase, the peptide is cleaved C-terminal to the chemically modified residue to produce LKRAJ (SEQ ID NO:5, where "J" is 2-aminoethanethiol) and LG (SEQ ID NO:6; see Table 3; SEQ ID NOS:5-12).

A method of the invention can be performed, for example, by treating a sample that includes at least one peptide with one or more reagents that can chemically modify a PTM amino acid residue in the peptide, and containing the chemically modified amino acid residue(s) with a proteolytic agent that can specifically cleave the peptide at the position(s) of a chemically modified amino acid residue to produce cleavage products indicative of the position(s) of a PTM amino acid residue in the peptide. As used herein, the term "post-translationally modified amino acid residue" or "PTM amino acid residue" is used according to its commonly understood meaning of an amino acid residue in a peptide that is modified following translation of the peptide. Post-translational modifications, which can be effected in a cell following translation of the peptide or can be effected using chemical methods on an isolated peptide, are well known in the art, and include, for example, phosphorylation, in which a phosphate group is added by a kinase or a chemical reaction to the hydroxyl position of a serine, threonine, or tyrosine; acetylation, in which an acetyl group is added by an acetylase or a chemical reaction to a free amino group (e.g., at an amino terminus of a peptide or to the epsilon amino group of lysine); farnesylation, in which a farnesyl group is added to a peptide containing a C-terminal CAAX (SEQ ID NO:31) motif or to the sulfhydryl group of cysteine; and glycosylation, in which one or more sugars or sugar derivatives (e.g., glucose, glucosamine, galactose, galactosamine, mannose, fucose, and/or sialic acid), including oligosaccharides and polysaccharides, is added by a glycosylase or a chemical reaction to an asparagine (N-linked glycosylation), or to hydroxylysine, or serine or threonine (O-linked glycosylation).

The term "chemically modified amino acid residue" is used herein to refer to a PTM amino acid residue of a peptide that has been treated with one or more reagents such that the post-translational modification is changed or removed from the amino acid residue. As a result of such a chemical modification according to the present methods, the peptide at the position of the chemically modified amino acid residue is rendered susceptible to cleavage by a proteolytic agent, wherein the peptide was not previously susceptible to cleavage by the proteolytic agent at that position. Phosphoserine, phosphothreonine, O-glycosylserine, and O-glycosylthreonine provide examples of PTM amino acid residues that can be chemically modified by a β-elimination, Michael addition, to produce a lysine analog, which renders a peptide susceptible to proteolytic cleavage to a lysine endopeptidase C-terminal to the lysine analog.

Phosphoserine, phosphothreonine, O-glycosylserine, and O-glycosylthreonine, when exposed to basic conditions, yield an alanine derivative (i.e., dehydroalanine, β-methyldehydroalanine, aminoalanine, and β-methyl-aminoalanine, respectively; see, e.g., Scheme 1).[10,11,16] By carrying out the elimination reaction in the presence of a strong nucleophile such as 2-aminoethanethiol (2-AET; see Scheme 1, reaction 2), a lysine analog, (e.g., 2-aminoethylcysteine; structure 2) is generated. This product is identical to that obtained by reacting cysteine amino acid with ethyleneimine or N-(iodoethyl) trifluoroacetamide.[23-26] These latter reactions, which are well known in protein chemistry, convert cysteine residues to a structural analog of lysine, thereby introducing a new protease-sensitive cleavage site for trypsin or for a lysine endopeptidase where a cysteine residue formerly existed.[27] In the case of lysyl endopeptidase, the 2-aminoethylcysteine site is cleaved with rates comparable to that of lysine.[25]

SCHEME 1

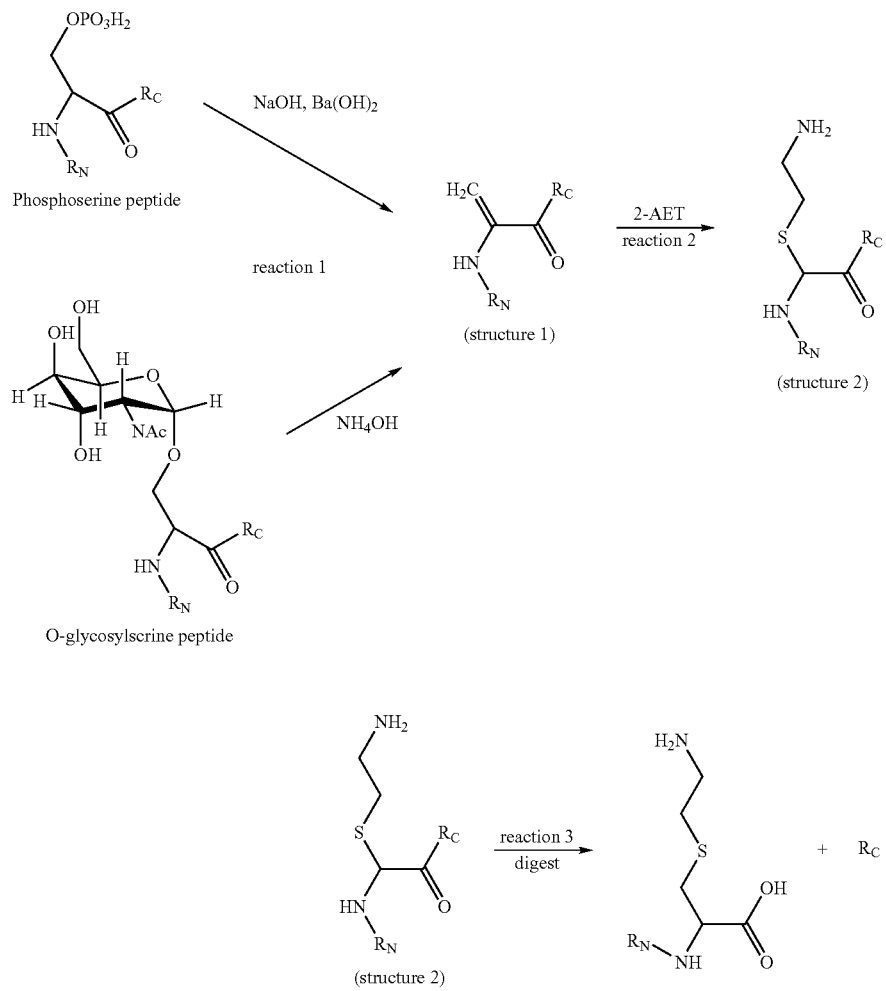

There has been little information regarding β-elimination reactions of phosphothreonine, though some evidence has indicated that dehydrobutyric acid (intermediate in Scheme 2) is the reaction product.[11] Similar chemistries have been reported for facilitating mass analysis.[11,16] As disclosed herein, the β-methyl derivative (β-methyl-2-aminoethylcysteine) as shown in Scheme 2 constitutes a product of this reaction, and chemical modification of phosphothreonine allows exploitation of the specificity of a proteolytic enzyme, thus allowing identification of the position and identity of the phosphoamino acid residue in a peptide (see Example 1, and Rusnak et al., supra, 2002; see, also, Knight et al., *Nat. Biotechnol.* 21:1047-1054, 2003, which is incorporated herein by reference). The present methods are further applicable to the analysis of O-glycosylated peptides, which undergo the same β-elimination as phosphopeptides.[11,16]

Information regarding the site and extent of post-translational modification can be ascertained either by N-terminal analysis of the sequence immediately C-terminal to the site of the chemically modified (formerly PTM) amino acid residue, or by MS of the digest peptides and prior knowledge of the protein sequence. In addition, multiple parallel analyses can be performed without the need for peptide separation. If N-blocking with a suitable reagent is carried out before chemical modification, digestion generates new amino termini C-terminal to the sites of modification. Simultaneous chemical sequencing and/or MS allows immediate identification of the modified amino acid residues by comparison with the known protein sequence.

A method of the invention can be performed, for example, by contacting PTM peptides containing, or suspected of containing, one or more phosphorylated and/or O-glycosylated serine and/or threonine residues with a reagent (e.g., a base such as NaOH, Ba(OH)$_2$, and/or NH$_4$OH; or boron-ammonia complex in aqueous ammonia; see Huang et al., *Rapid Comm. Mass Spec.* 16:1199-1204, 2002, which is incorporated herein by reference) that effects a β-elimination to convert the phosphorylated and/or glycosylated residue(s) (e.g., serine or threonine) to an alanine derivative, and a reagent that effects a Michael addition (e.g., 2-AET) to convert the alanine derivative to a 2-aminoethylcysteine derivative (see, Example 1; see, also, Rusnak et al., supra, 2002). If desired, the peptides can be coupled to a solid support (e.g., a surface of a bead, chip, plate, or glass slide) prior to the

SCHEME 2

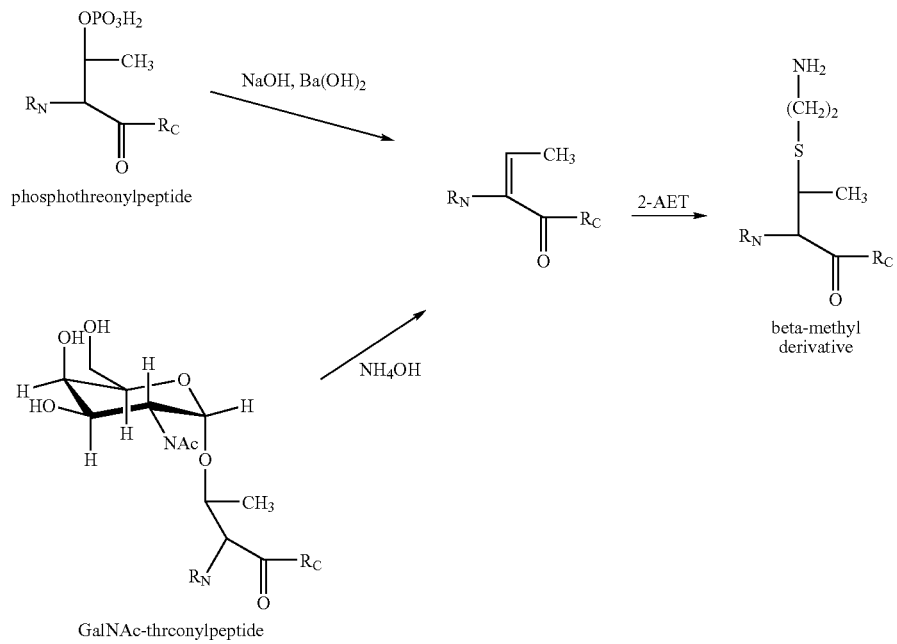

chemical modification. Coupling can be performed, for example, using carbodiimide, or a derivative thereof (e.g., EDC; 1-ethyl-3-(3-dimethylaminopropyl)-carbodiimide) in a water soluble reaction to link the peptides, via their N-termini, to beads containing carboxyl functional groups (see, e.g., Thompson et al., *Anal. Chem.* 75:3232-3243, 2003, which is incorporated herein by reference). An advantage of linking the peptides to be examined to a solid support is that, upon practicing a method of the invention, peptides that are not post-translationally modified remain attached to the support, whereas those that originally contained phosphorylated and/or O-glycosylated amino acid residues are cleaved at the PTM residue and the fragment(s) C-terminal to the N-terminal-most chemically modified residue is/are released from the support.

Where the peptide to be examined contains greater than about 20 amino acids (e.g., 25, 30, 35, 40, 50, 75, 100, 200, or more), the PTM polypeptide (protein) can be treated, prior to chemical modification, with a protease (e.g., trypsin, chymotrypsin, or Lys-C; see, e.g., Havlis et al., *Anal. Chem.* 75:1300-1306, 2003, which is incorporated herein by reference; see, also, below) or a chemical that specifically cleaves a peptide (e.g., cyanogen bromide, which cleaves at methionine residues; BNPS skatole, which cleaves at tryptophan residues; see, e.g., Hunziker et al., *Biochem. J.* 187:515-519, 1980, which is incorporated herein by reference); or thiocyanate which introduces an iminothiazolidine ring (Catsimpoolas and Wood, *J. Biol. Chem.* 241:1790-1796, 1966, which is incorporated herein by reference) to generate peptide fragments for examination. For example, where a CTID™ assay is to be performed and cleavage products are to be examined by mass spectrometry, it can be desirable to treat a protein with a protease or chemical that generates peptide fragments of less than about 2.5 kDa, which is an upper practical mass limit for mass spectrometric analysis. An enzyme such as trypsin, which cleaves at lysine and arginine, but not Lys-Pro bonds, can generate such peptide fragments, though it should be recognized that any Lys-Pro bonds in the peptide can be cleaved by Lys-C. As such, if Lys-C is used to cleave a peptide containing a chemically modified amino acid residue, it can be desirable to acetylate the peptide fragments in a sample following the trypsin cleavage (e.g., using O-methylisourea), and prior to contacting the peptides with Lys-C.

Peptide fragments produced following enzymatic or chemical treatment can, but need not, be separated (e.g., by mass, charge, or hydrophobicity) using a method such as liquid chromatography (e.g., FPLC or HPLC) or gel electrophoresis; a separation step is not necessary, for example, where multiple parallel analyses are to be performed (e.g., a multiplex analysis). For example, N-terminal blocking of the peptide fragments can be performed, wherein, following chemical modification and cleavage, new N-termini are generated C-terminal to the chemically modified (and cleaved) sites (i.e., the PTM residues); chemical sequencing or mass spectrometry (MS) then can be used to identify the modified amino acid residue where the sequence of the protein is known.

Peptide fragments of a protein can be obtained by contacting the protein (e.g., a phosphoprotein or a glycoprotein) with a chemical agent that cleaves one or more peptide bonds of the protein, or by contacting the protein with one or more proteases. A protease useful for generating peptide fragments of a protein can be an exopeptidase, which sequentially cleaves amino acid residues of the protein from the N-terminus (aminopeptidases) or from the C-terminus (carboxypeptidases), or can be an endopeptidase, which cleaves the protein N-terminal or C-terminal to one or a few specific amino acid residues. Endoproteases, and their cleavage specificity, are well known in the art, and include, for example, trypsin, which cleaves proteins C-terminal to lysine and arginine; chymotrypsin, which cleaves proteins C-terminal to tyrosine, tryptophan, phenylalanine, and methionine; pepsin, which preferentially cleaves proteins C-terminal to phenylalanine, leucine, and glutamic acid; endoprotease Asp-N, which cleaves proteins C-terminal to aspartic acid and glutamic acid; as well as the lysine endopeptidases, lysyl endopeptidase and Lys-C, which cleave specifically C-terminal to lysine residues. Where cleavage products are to be examined by mass spectrometry, and the sample contains peptides having a C-terminal lysine residue (e.g., peptide fragments generated by cleavage with an endopeptidase such as trypsin), the peptide(s) can be contacted with an agent that modifies a C-terminal lysine residue. Such agents, which include, for example, O-methylisourea or 2-methoxy-4,5-dihydro-1H-imidazole, can provide the advantage that they can increase the signal obtained using mass spectrometry.

The present methods can include a preliminary step of blocking one or more substrate amino acid residues in the peptide. When used with respect to the methods of the invention, the term "substrate amino acid residue" refers to an amino acid residue, other than a PTM amino acid residue to be examined, that presents a site in a peptide that can be cleaved by a proteolytic agent that is to be used in the method, or that is susceptible to being chemically modified by one or more reagents to be used such that the chemical modification would render the amino acid susceptible to cleavage by the proteolytic agent to be used. As such, a substrate amino acid residue can be any amino acid residue that is not a PTM amino acid residue. Where a peptide to be examined contains, or is suspected of containing, one or more amino acid residue(s) susceptible to being chemically modified by a first and/or second reagent, blocking of the substrate amino acid residue can be performed prior to contacting the sample with the reagent. For example, where the method utilizes a reagent containing 2-AET, and the peptide contains cysteine(s), which can be chemically modified by 2-AET, the cysteine(s) can be blocked prior to treating the sample with 2-AET. Similarly, where the peptide contains an amino acid residue susceptible to cleavage by a proteolytic agent to be used in the method, blocking of the substrate amino acid residue is performed prior to contacting the peptide with the proteolytic agent. For example, where the method utilizes lysyl endopeptidase as the proteolytic agent, and the peptide contains lysine, which can act as a substrate for cleavage by lysyl endopeptidase, the lysine residue(s) can be blocked prior to contacting the peptide with the lysyl endopeptidase (e.g., prior to treating the sample with the first and/or second reagent).

A substrate amino acid can be blocked using any means typically used to decrease the reactivity of an amino acid side chain or to render an amino acid residue of a peptide resistant to a proteolytic agent. For example, substrate amino acid residues can be blocked using compounds that are used to protect amino acid side chains from reacting during chemical synthesis of peptides (e.g., using a tert-butyl group to block a carboxyl, hydroxyl, or sulfhydryl side chain; or a trityl group to block an amide or the histidine imidazole side chain; or Pmc to block the arginine side chain), or can be blocked by acetylating the substrate amino acid residue(s), provided the PTM amino acid residue to be identified is not an acetylated amino acid residue.

In one embodiment of a method of the invention, β-elimination and Michael addition reactions are used convert a phosphorylated or O-glycosylated serine or threonine residue to a 2-aminoethylcysteine derivative, which is a substrate for cleavage by a lysine endopeptidase. As such, following chemical modification, the peptides can be contacted with a lysine endopeptidase (e.g., *Achromobacter lyticus* lysyl endopeptidase—E.C. 3.4.21.50; or *Lysobacter enzymogenes* endoprotease Lys-C), which cleaves the peptides N-terminal to the modified amino acid residue(s). Where the peptide to be examined contains, or is suspected of containing, lysine residues, the substrate lysine residues can be blocked, for example, by acetylation (e.g., using N-acetoxysuccinimide), thus preventing cleavage by a lysine endopeptidase. Further, as mentioned above, where a protein is cleaved prior to examination according to the present methods, using an enzyme such as trypsin, which cleaves at and leaves C-terminal lysine residues, the C-terminal lysine residues can be modified, for example, by conversion to homoarginine (e.g., using O-methylisourea or 2-methoxy-4,5-dihydro-1H-imidazole). Such peptides containing C-terminal homoarginine (rather than lysine) provide enhanced MS signals.

Following cleavage with the lysine endopeptidase, one or more cleavage products can be examined to determine the position and/or identity of the PTM amino acid residue(s). For example, the cleavage products can be examined by MS, wherein the mass of the cleavage products provide an indication of the position(s) of the cleavage site(s) and, therefore, the PTM amino acid residue(s). Where the sequence of the peptide, or a protein from which the peptide was derived, is known, the identity of the amino acid residue can be determined based on the cleavage position. One or more cleavage products, or a portion thereof, also can be sequenced using chemical methods. For example, Edman degradation can be used to determine the N-terminus of the cleavage product C-terminal to the cleavage site, thus allowing a determination of the position of the PTM amino acid residue and, where the sequence of the peptide (or protein) is known, identification of the PTM amino acid residue.

The methods of the invention provide a convenient and effective means for identifying and characterizing serine and threonine phosphorylation and O-glycosylation sites in peptides. For example, by identifying the mass of the products of digestion, or the amino acid sequence immediately C-terminal to the modified amino acid, the site can be ascertained quickly when the sequence of the protein from which the peptide is derived is known. Further, when chemical modification of a PTM amino acid residue and cleavage is performed in a buffer such as N-methylpiperidine acetate buffer, chemical sequencing can be performed without a need to purify or desalt the cleavage products (see Example 1). As such, the methods can be used to determine multiple sites using a conventional method such as chemical sequencing or MS without the necessity of performing a separation step before analysis. Further, if the peptide(s) only contain a few post-translationally modified sites, identification of the modified amino acid residues can be determined by simple inspection.

In addition to allowing for the identification of the position(s) of PTM amino acid residue(s) in a peptide, the present methods also allow for the identification of the particular amino acid residue (e.g., that a phosphorylated amino acid residue in threonine). Identification of the particular amino acid residue is facilitated when the sequence of the peptide, or of the protein from which a peptide is derived, is known. Direct database searching of protein sequences employing multiple sequencing yields has been achieved using algorithms developed for this task.[35] Graphical analysis of N-terminal sequencing data also can be used to provide information about the relative abundance of the modifications. For optimal results with Edman sequencing, lysine side chains and the amino terminus can be quantitatively blocked, yielding a single product. As disclosed herein, N-acetoxysuccinimide gave a high degree of acetylation, and multiple acetylations were observed occasionally. While over-acetylation can sometimes require that a separation step be performed to avoid overly complex mass spectra, it is not expected to interfere with the few cycles of Edman degradation required to specify phosphorylation and/or glycosylation sites. Further, when the sequence of the protein is known, the acetylation reaction need not proceed to 100% completion in order to obtain useful results because residue yields C-terminal to all of the lysine cleavage sites are predictable from the known sequence and, therefore, can be subtracted from the result.

Limited conversion of a phosphoamino acid to its 2-aminoethylcysteine derivative should not affect the identification of the site because peptide that is not converted is not a substrate for the peptidase and therefore, is not expected to yield a signal. However, non-specific cuts can contribute to the background, hindering identification of a PTM amino acid residue when the peptide is not known. As disclosed herein, the present methods can be performed using low concentrations of protease and relatively short digestion times when chemical background is a concern. Using the exemplified conditions (see Example 1), no nonspecific cleavage events were detected, and no sequences from peptidase autolysis were observed.

It also is recognized that amino acid residues in the vicinity of lysine can result in slower kinetics for the enzymatic cleavage. For example, sites with proline, glutamate, or aspartate C-terminal to the target amino acid (e.g., a phosphoamino acid) generally are expected to hydrolyze with slower kinetics than peptides containing other amino acid residues at this position. Slower kinetics also would be expected for digestion of the 2-aminoethylcysteine by trypsin.[25] Indeed, in the case of the PS peptide (SEQ ID NO:1), only a cut at Arg-3 was observed with trypsin. Lysyl endopeptidase also cleaves at lysines that are followed by proline[36], but with slower kinetics. In such cases, the time of digestion can be varied to obtain satisfactory cleavage.

The present methods can be particularly useful for characterizing large, difficult to analyze peptides where the object of study has been well developed experimentally. For example, such large target peptides can be studied under various cellular conditions by the present chemical procedures.

In practicing the present methods, the peptide containing the PTM amino acid residue can be coupled to a solid support. The solid support can be any solid material to which a peptide can be coupled directly (e.g., via a terminal amino or carboxy group) or indirectly (e.g., via a linker molecule), and that is stable to the conditions under which the method steps are performed (e.g., stable to basic conditions). For example, the solid support can be a bead (e.g., a plastic bead or an agarose-based bead), which can further include a magnetic material; a glass slide; a well, or a chip (e.g., a silicon wafer). Because only a peptide containing a PTM amino acid residue is cleaved by a proteolytic agent according to the present methods, an advantage of coupling peptides to be examined to a solid support is that peptides that do not contain a PTM amino acid residue remain bound to the support, whereas cleavage products of peptides containing a PTM amino acid residue are released from the support, thus facilitating detection of the cleavage products.

The methods of the invention can be performed in any of various formats, including, for example, as a single assay of a single peptide (i.e., a homogenous population of the same peptide); or in a multiplex format, wherein a plurality of peptides (e.g., proteolytic fragments of a protein) is examined in a single sample. The use of mass spectrometry to analyze cleavage products (or uncleaved peptides) can be particularly useful for performing a multiplex analysis because mass spectrometry can readily detect small molecular mass differences between peptides/cleavage products of a mixed population and, therefore, can detect several different peptides/cleavage products in a single run. Further, the methods conveniently can be adapted to and performed in a high throughput format, wherein a plurality of samples, some or all of which can contain one peptide or a plurality of peptides, can be examined in parallel.

High throughput (or ultrahigh throughput) assays provide the advantage that numerous samples can be examined in parallel, thus allowing, for example, for the inclusion of appropriate controls, or for the examination of several different samples under substantially identical conditions, or for the examination of several same samples under different conditions. Further, high throughput assays are readily adaptable to automation, thus reducing costs, as well as reducing the potential for random errors. A high throughput assay can be performed, for example, in wells of a plate (e.g., 96 well, 384 well, or 1536 well plates), or in delineated regions (e.g., 10, 100, 1000, 10,000, or 100,000 delineated regions) of a chip or glass slide. For example, a solid support such as a silicon based chip or glass slide can be modified to contain pits, into which a sample can be deposited, or to contain functional linker molecules, wherein samples containing peptides to be examined can be deposited in specified positions (e.g., robotically) such that the peptides are coupled to the support. In one embodiment, the samples are deposited in a defined pattern such as array, which can be an addressable array. An addressable array can facilitate identification of particular samples, as well as automation of the types, times, and amounts of one or more reagents, proteolytic agents, and the like added to and/or removed from the sample, and examination of the cleavage products produced according to the methods.

The present invention also relates to a kit, which contains components useful for identifying a position of a PTM amino acid residue in a peptide. A kit of the invention can contain, for example, a reagent that effects β-elimination of a phosphoserine, phosphothreonine, O-glycosylserine, or O-glycosylthreonine residue of a peptide to produce an amino acid analog Michael acceptor (e.g., sodium hydroxide, barium hydroxide, ammonium hydroxide, or boron-ammonia complex in aqueous ammonia); a reagent that includes a nucleophile that can interact with the amino acid Michael acceptor to produce a chemically modified amino acid residue in a peptide (e.g., an amine or a thiol); and a proteolytic agent that can cleave a peptide at a position of a chemically modified amino acid residue formed by β-elimination and Michael addition of the chemically modified residue (e.g., an enzyme). In one embodiment, the kit contains two or more reagents that effect β-elimination, and/or two or more nucleophile that can interact with the amino acid Michael acceptor (e.g., 2-AET, and 1,2-DAE); and/or two or more proteolytic agents (e.g., lysyl endopeptidase, and Lys-C), such a kit allowing the user an option of selecting one or more components for a particular assay.

A kit of the invention also can contain one or more other component(s) that can be useful for practicing the present methods and/or analyzing the results. For example, the kit can contain a component that can be useful as a control, or for standardizing an assay, (e.g., a peptide that contains at least one phosphoamino acid residue, a peptide that contains at least one O-glycosylated amino acid residue, a peptide that contains at least one phosphoamino acid and at least one O-glycosylated amino acid residue, or a combination of such peptides). The kit also can contain, for example, one or more glycosidases, one or more phosphatases, or a combination of glycosidase(s) and phosphatase(s).

The following examples are intended to illustrate but not limit the invention.

EXAMPLE 1

Chemically Targeted Identification of Phosphoamino Acids and O-Glycosylated Amino Acids in Peptides This example demonstrates that chemical modification of post-translationally modified amino acids in peptides and cleavage at the position of the chemically modified amino acid residues allows the identification of phosphorylated and glycosylated amino acid residues in peptides.

Phosphatase substrate (PS) and protein kinase C substrate (PKC) phosphopeptides were obtained from Anaspec Labs (San Jose, Calif.). Calcineurin substrate (CNS) was obtained from Calbiochem (San Diego, Calif.). Lysyl endopeptidase from *Achromobacter lyticus* (E.C. 3.4.21.50) was purchased from WAKO Chemicals (Richmond, Va.). N-Hydroxysuccinimide and 2-amino-ethanethiol hydrochloride (2-AET) were from Sigma-Aldrich Chemical Co. (St. Louis, Mo.). The O-threonine glycosyl peptide was obtained from Nathan Lamarre-Vincent of the Hsieh-Wilson laboratory at Caltech (Pasadena, Calif.). The O-serine glycosyl peptide was the gift of Dr. Gemma Arsequell (Consejo Superior de Investigaciones Cientificas, Centro do Investigacion y Desarrollo, Unit of Glycoconjugate Chemistry; Barcelona, Spain). All chemicals were reagent grade and were used without further purification.

N-Acetoxysuccinimide was synthesized according to the method of Geng et al.[28] Acetylation was carried out essentially according to the procedure of Ji et al.[29] A 10-fold to 50-fold molar excess of the reagent over free amine was added to the peptide solution containing 0.1 M phosphate buffer, pH 7.4. Peptides were incubated overnight at room temperature. After reversed-phase purification, acetylated peptides were converted to their 2-aminoethylcysteine derivatives using NaOH with saturated $Ba(OH)_2$ by including 2-AET in the mixture.[30] Peptides were incubated 4-6 hr at 45-47° C. in a solution containing 10 μl of 1 M NaOH, 3 μl of a saturated solution of $Ba(OH)_2$, and 15 μl of 0.5 M 2-AET. The O-glycosylated peptides were incubated for 5-12 hr at 45° C. in 25% $NH_4OH$ containing 0.14 M 2-AET. After reversed-phase desalting, the modified peptides were digested with *Achromobacter* lysyl endopeptidase in 0.05 M N-methylpiperidine acetate buffer, pH 9, or 0.05 M Tris-HCl, pH 9.2, for 1 hr at 45° C.

Peptides digested in the N-methylpiperidine buffer could be loaded directly onto the sequencer. For analysis by matrix-assisted laser desorption/ionization time-of-flight (MALDI-TOF) MS, the digest was desalted with the use of a C18 ZipTip™ column (Millipore Corp.; Bedford Mass.) and the peptides were eluted directly to the target in 50% acetonitrile containing the appropriate matrix. In some cases, in-source or post-source decay fragmentation with MALDI MS or tandem MS was used to check the sequence.[31–33] In the case of the 2-aminoethylcysteine-derivatized calcineurin substrate peptide, the products of digestion were analyzed directly by Edman degradation with no desalting or purification.

The entire chemical procedure was also carried out on the peptide coupled covalently to an arylamine poly-vinylidene difluoride (AA-PVDF) membrane. Edman degradation was carried out with a PROCISE 492 cLC protein sequencer (Applied Biosystems, Inc.; Foster City Calif.) as previously described.[34]

Experiments were carried out using phosphoseryl, phosphothreonyl, and O-threonine and serine glycosylated peptides. CNS peptide (SEQ ID NO:3; see Table 1) was selected because it contains one phosphoserine in a position that would generate a short C-terminal peptide and, thus, can present a challenge for N-terminal sequencing. PKC peptide (SEQ ID NO:2) was selected because it contains two lysines, so that efficient side chain blocking would be required. PS peptide (SEQ ID NO:1) contains one lysine and a single phosphothreonine (see Table 1; SEQ ID NOS:1-4; also listing calculated monoisotopic masses of peptides). The procedure also was applied to a nonstandard, expressed glycosylated peptide that contains multiple serine and threonine residues as potential sites of the post-translational modification.

Figure 2:
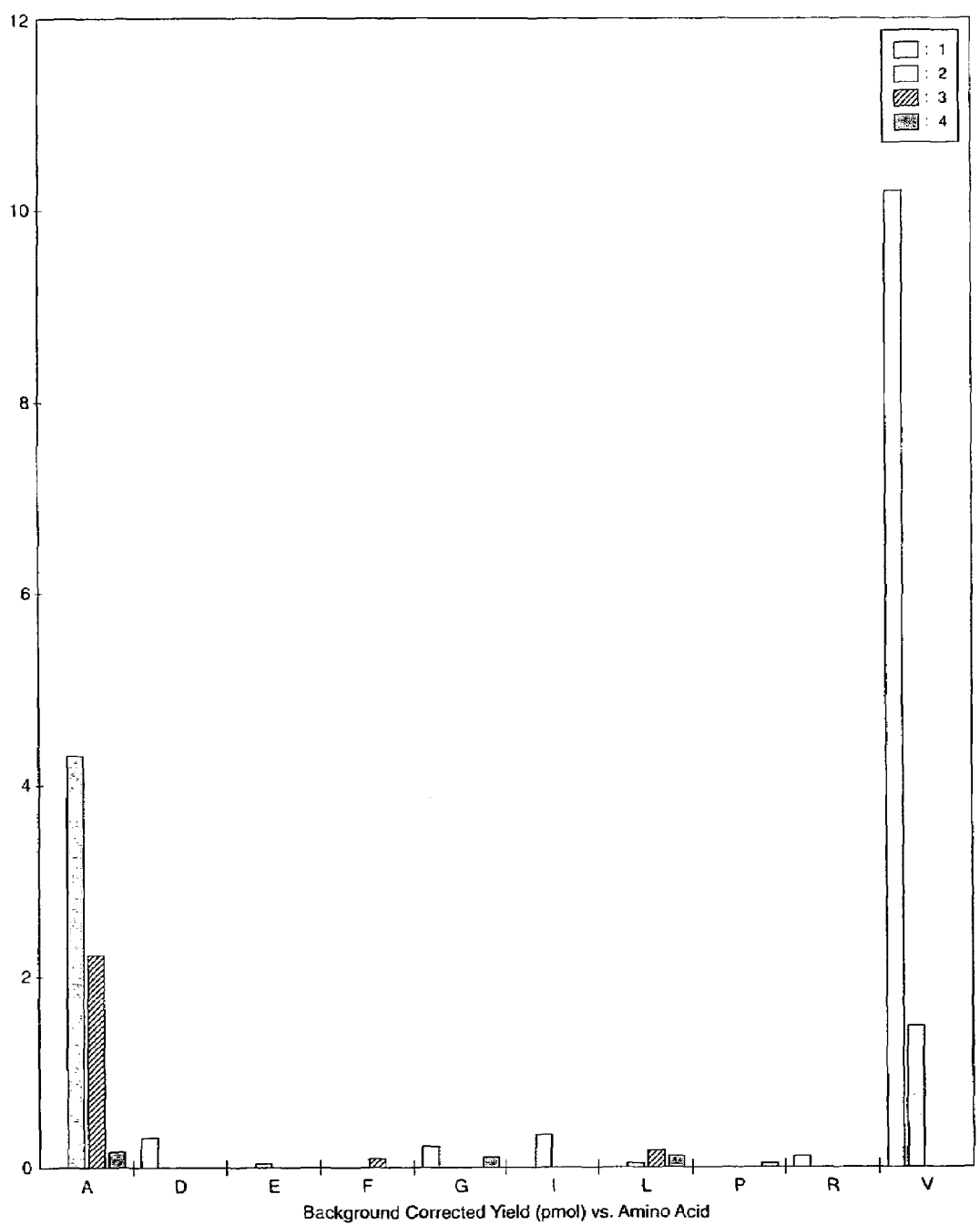
FIG. 2 shows PTH-amino acid yields from four cycles of Edman degradation of acetylated and converted CNS peptide (SEQ ID NO:3). All amino acid residues potentially yielded from the peptide composition are shown. The sequence VAAE (SEQ ID NO:10) was read. Note the complete absence of the original native-N-terminal sequence DLDVP (SEQ ID NO:13).

The acetylated and 2-aminoethylcysteine products were confirmed by MS (see Table 2). In-source decay (ISD) MALDI-TOF MS was carried out on the unacetylated, 2-AET-modified, CNS peptide. ISD data yielded the partial sequence FDRRVJ(VA)AE (SEQ ID NO:32), where J had a mass of 146.7 Da (146.2 Da calculated for 2-aminoethylcysteine; see FIG. 1). Following cleavage with lysyl endopeptidase, products were confirmed by either MS or N-terminal sequencing (Table 3). Edman sequencing of the unpurified digest mixture of CNS peptide revealed a single sequence, VAA (SEQ ID NO:33; see FIG. 2), which corresponded to that immediately C-terminal to Ser-14, identifying this residue as the site of phosphorylation. The yield of C-terminal Glu was not significant due to washout. Additionally, the cleavage products of CNS peptide showed a single ion at 1843.1 Da, in good agreement with the calculated mass of 1843.0 Da predicted for the N-acetylated N-terminal portion DLDVPIPGRFDRRJ (SEQ ID NO:9; see Table 3; SEQ ID NOS:5-12).

A second experiment was performed in which the peptide was coupled to an arylamine membrane, acetylated, converted to the 2-aminoethylcysteine derivative, and then digested with lysyl endopeptidase. Digestion was carried out for 110 min at 45° C., and the sequence VAAE (SEQ ID NO: 10) was read. Although the yield of C-terminal Glu increased, some coupling of the γ-carboxyl probably occurred. In addition, some N-terminal residues (except Asp) were also observed, and artifact peaks were observed in the chromatograms, possibly resulting from the action of the strong base on the membrane (not shown). The

TABLE 1

Peptides for Conversion to Endopeptidase-Susceptible Sites

| Peptide | Amino acid sequence | Calc. |
| --- | --- | --- |
| PS | LKRApTLG-NH$_2$ | 836.46 |
| PKC | KRPpSQRHGSKY-NH$_2$ | 1421.70 |
| CNS | DLDVPIPGRFDRRVpSVAAE | 2191.08 |
| O-GlcNAc-serine peptide | FAASNYPAL | 1155.54 |

PS, phosphatase substrate peptide; PKC, phosphorylated protein kinase C substrate peptide; CNS, calcineurin substrate peptide.

TABLE 2

Observed and Calculated Monoisotopic Masses for Native Peptides and Their Acetylated and 2-Aminoethyl Derivatives[a]

| | Native | | Acetylated | | 2-Aminoethyl | |
| --- | --- | --- | --- | --- | --- | --- |
| Peptide | Calc. | Obs. | Calc. | Obs. | Calc. | Obs. |
| PS | 836.5 | 836.5 | 920.5 | 920.6 | 899.5 | 899.6 |
| PKC | 1421.7 | 1421.7 | 1547.7 | 1547.7 | 1526.8 | 1526.8 |
| CNS | 2191.08 | 2191.1 | 2233.1 | 2233.1 | 2212.1 | 2212.1 |
| O-hexSer | 1155.54 | 1155.5 | [b] | [b] | 1011.48 | 1011.5 |

PS, phosphatase substrate peptide; PKC, phosphorylated protein kinase C substrate peptide; CNS, calcineurin substrate peptide.
[a]Phosphopeptides were N-acetylated with N-acetoxysuccinimide, converted to the 2-amino-ethyl derivative, purified by reversed-phase HPLC, and analyzed by MALDI-TOF MS.
[b]Peptide not acetylated.

TABLE 3

Fragments from Lysyl Endopeptidase Digestion[a]

| Peptide | N-Terminus | | | C-Terminus | | |
|---|---|---|---|---|---|---|
| | Sequence | Calc. | Obs. | Sequence | Calc. | Obs. |
| PS | LKRAJ[b] | 730.4 | 730.5 | LG | 187.1 | not obs. |
| PKC | KRPJ | 629.3 | 629.4 | QRHGSKY[c] | 915.5 | 915.6 |
| CNS | DLDVPIPGRFDRRJ | 1841.9 | 1842.1 | VAAE[c] | 388.2 | not obs. |
| O-hexSer | FAAJ | 453.2 | 453.2 | NYPAL | 576.3 | 576.3 |

PS, phosphatase substrate peptide; PKC, phosphorylated protein kinase C substrate peptide: CNS, calcineurin substrate peptide.
[a]Peptides were modified as described in the Materials and Methods section, digested with lysine endopeptidase, and analyzed by MALDI-TOF MS.
[b]J, 2-aminoethanethiol modified residue.
[c]Sequences QRHGSKY and VAAE were determined by Edman degradation.

Figure 3:
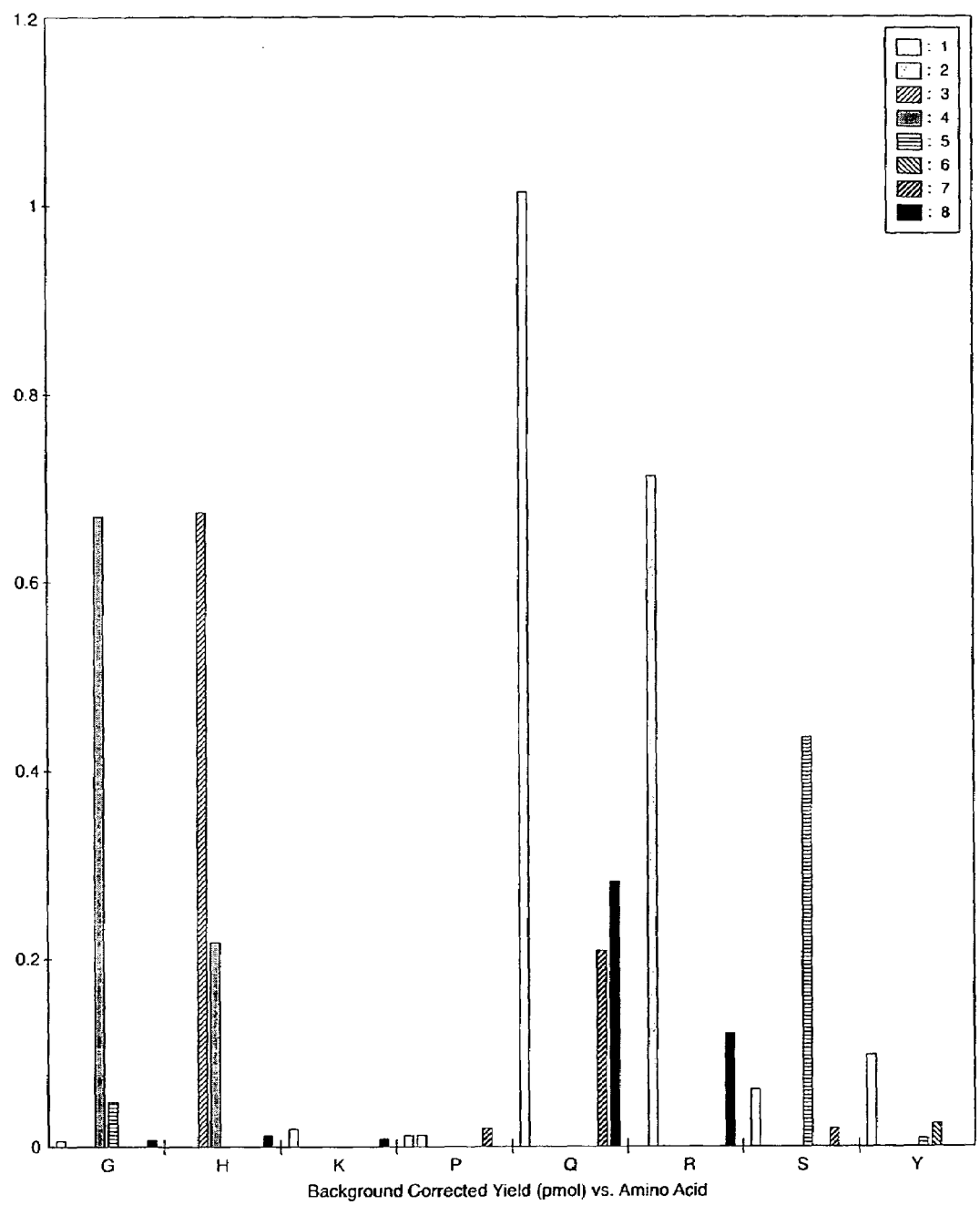
FIG. 3 shows PTH-amino acid yields from eight cycles of Edman degradation of acetylated and converted PKC peptide (SEQ ID NO:2). All amino acids potentially yielded from the peptide composition are shown. The sequence QRHGS(acK) (SEQ ID NO:14; "ac" indicates acetylated; "acK" is acetylated lysine) was read. PTH-εN-acetyllysine eluted as a peak with retention time 0.2 min earlier than PTH-Ala Note the complete lack of PTH-Lys in the first cycle.

2-aminoethylcysteine derivative of acetylated PKC peptide was purified by high-performance liquid chromatography (HPLC), digested, and a portion desalted by reversed phase. Two peptides were detected by MS at 915.6 Da and 629.4 Da, in addition to unreacted 1526.9 Da ion. The two fragments were in good agreement with values calculated for the fragments (see Table 3). PKC peptide digest (3 µmol) was applied directly to the sequencing disk and sequenced without purification. A single sequence, QRHGS(acK) (SEQ ID NO:14), corresponding to the residues C-terminal to phosphoserine residue 4 (see FIG. 3) was observed. Residue 10, PTH-εN-acetyllysine, was detected as a peak that eluted at a retention time 0.2 min less than PTH-Ala.

To determine whether the method could be used to identify phosphothreonine residues, the procedure was carried out on PS peptide (SEQ ID NO:1). HPLC purification of the reaction products with mass analysis of peak fractions showed about 50% conversion to the β-methyl-aminoethylcysteine peptide. The HPLC fraction was divided into two aliquots, and each was digested separately with trypsin or with lysyl endopeptidase. Anticipating washout due to the short C-terminal sequence LG-NH$_2$ (SEQ ID NO:7) the products were characterized by MS. Analysis of the HPLC-purified product from the tryptic digestion yielded only the ion at 500.3 Da, which corresponded to the sequence (acL)(acK)R (SEQ ID NO:34). Analysis of the lysyl endopeptidase digest from the HPLC purification yielded an early-eluting peak with mass 730.45 Da, which is in good agreement with the value of 730.41 Da calculated for the sequence (acL)(acK)RAJ (SEQ ID NO:35), where J is the β-methyl-aminoethylcysteine derived from threonine 5 of the peptide (see Table 3).

The procedure also was carried out on a peptide that contained a serine residue that was glycosylated. Analysis of the digestion of this material revealed a C-terminal peptide product with mass 1155.5 Da, thus fixing the site of the glycoside to the serine residue in the peptide. This result indicates that the site of modification can be assigned solely on the basis of the mass spectrometry result. The digest was also sequenced directly without purification, and both N-terminal and C-terminal sequences were confirmed.

These results demonstrate that phosphorylated and glycosylated amino acid residues can be identified and localized in peptides.

REFERENCES

Each of the following articles is incorporated herein by reference.

1. Helmbrecht et al., *Cell Proliferation* 2000; 33:341-365.
2. Herrington et al., *Oncogene* 2000; 19:2585-2597.
3. Dufner and Thomas, *Exp Cell Res* 1999; 253:100-109.
4. Pause et al., *Nature* 1994; 371:762-767.
5. Dell and Morris, *Science* 2001; 291:2351-2356.
6. Haltiwanger et al., *Biochem Biophys Res Commun* 1997; 231:237-242.
7. Hart, *Annu Rev Biochem* 1997; 66:315-335.
8. Torres and Hart, *J Biol Chem* 1984; 359:3308-3317.
9. Sullivan and Wong, *Anal Biochem* 1991; 197:65-68.
10. Meyer et al., *FEBS Lett* 1986; 204:61-66.
11. Rademaker et al., *Anal Biochem* 1998; 257: 149-160.
12. Tomita and Marchesi, *Proc Natl Acad Sci USA* 1975; 72:2964-2968.
13. Gerken et al., *J Biol Chem* 1997; 272:9709-9719.
14. Annan et al., *Anal Chem* 2001; 73:393-404.
15. Chalkley et al., *J Am Soc Mass Spectrom* 2001; 12:1106-1113.
16. Greis et al., *Anal Biochem* 1996; 234:38-49.
17. Goshe et al., *Anal Chem* 2002; 74(3):607-616.
18. Carr et al., *Anal Biochem* 1996; 239: 180-192.
19. Annan and Carr, *Anal Chem* 1996; 68:3413-3421.
20. Liao et al., *Anal Biochem* 1994; 219:9-20.
21. Yuliang et al., *Rapid Commun Mass Spectrom* 2001; 15:1693-1700.
22. Adamczyk et al., *Rapid Commun Mass Spectrom* 2001; 15:1481-1488.
23. Cole, *Methods Enzymol.* 1967; 11:315-317.
24. Rall et al., *Biochemistry* 1969; 8:2486-2496.
25. Masaki et al., *Biosci Biotech Biochem* 1994; 58(1):215-216.
26. Schwartz et al., *Anal Biochem* 1980; 106:43-48.
27. Kawata et al., *Eur J Biochem* 1988; 176:683-697.
28. Geng et al., *J. Chromatogr* (A) 2000; 870:295-313.
29. Ji et al., *J. Chromatogr* (B) 2000; 745:197-210.
30. Molloy and Andrews, *Anal Chem* 2000; 73:5387-5394.
31. Katta et al., *Anal Chem* 1998; 70:4410-4416.
32. Brown and Lennon, *Anal Chem* 1995; 67:3990-3999.
33. Zhou et al., *Rapid Commun Mass Spectrom* 2000; 14:432-438.

34. Rusnak and Hathaway, *J Biomol Tech* 2001; 12:39-42.
35. Henzel et al., *Anal Biochem* 1999; 267:148-160.
36. Sakiyama and Masaki, "Lysyl endopeptidase". In Barrett A J, Rawlings N D, Woessner J F (eds): *Handbook of Proteolytic Enzymes*. San Diego, Calif.: Academic Press, 1998:261-263.

EXAMPLE 2

Chemically Targeted Identification of Phosphoamino Acids in a Phosphoprotein

This Example demonstrates that the chemically targeted identification method can be extended to the examination of phosphoproteins.

Post-translationally modified peptides often fail to give complete product ion spectra by tandem mass spectrometry, with increasing peptide chain length exacerbating the problem to the point where little or no useable structural information is obtained. In order to determine whether the chemically targeted identification method could be used to analyze longer peptides, the method was applied to a β-casein tryptic digest. Precursor ion and neutral loss analysis detected multiple peptides. Three sites were positively identified, including residues 15, 17, and 35, and two additional phosphorylations were inferred from peptide mass in the multiply phosphorylated N-terminal region of β-casein.

β-casein peptides were prepared by denaturing β-casein in freshly deionized 8M urea at 37° C. for 20 min, then diluting the sample to 2M urea, and digesting with trypsin in 0.1 M ammonium bicarbonate buffer at pH 8 overnight at room temperature (RT). β-elimination and addition reactions were performed as described in Example 1. Briefly, the β-casein peptide digest was modified in 1.0 N NaOH with 0.2M 2-AET at RT for up to 4 hr. Aliquots were removed at various intervals, diluted and analyzed by MALDI-TOF mass spectrometry using 2,5-dihydroxybenzoic acid matrix. The digest was desalted using a C18 guard cartridge dried in a SpeedVac™ centrifuge. The dry pellet was resuspended in a minimal volume, treated with 3% hydrogen peroxide for 3-5 min at RT, and dried. The sample was resuspended in water and analyzed by mass spectrometry.

Mass analysis was carried out using a Voyager DE™ STR MALDI-TOF mass spectrometer (Applied Biosystems, Inc.). Product ion analysis was performed on a QSTAR®-pulsar hybrid mass spectrometer (Applied Biosystems, Inc.). Linked scans, neutral loss or precursor ion, were carried out with an API 365 triple quadrupole LC/MS/MS mass spectrometer (Applied Biosystems, Inc.).

The sequence for β-casein (SEQ ID NO:15) is shown in Table 4 (below). Calculated masses for the β-casein peptides, including SEQ ID NO:16 (corresponding to amino acid residues 1 to 25 of β-casein; SEQ ID NO:15), and SEQ ID NO:21 (corresponding to amino acid residues 33 to 48 of β-casein; SEQ ID NO:15), are shown, including predicted masses depending on whether phosphoserine ("S") or the chemically modified 2-aminoethylcysteine ("X") residue is present.

Figure 4:
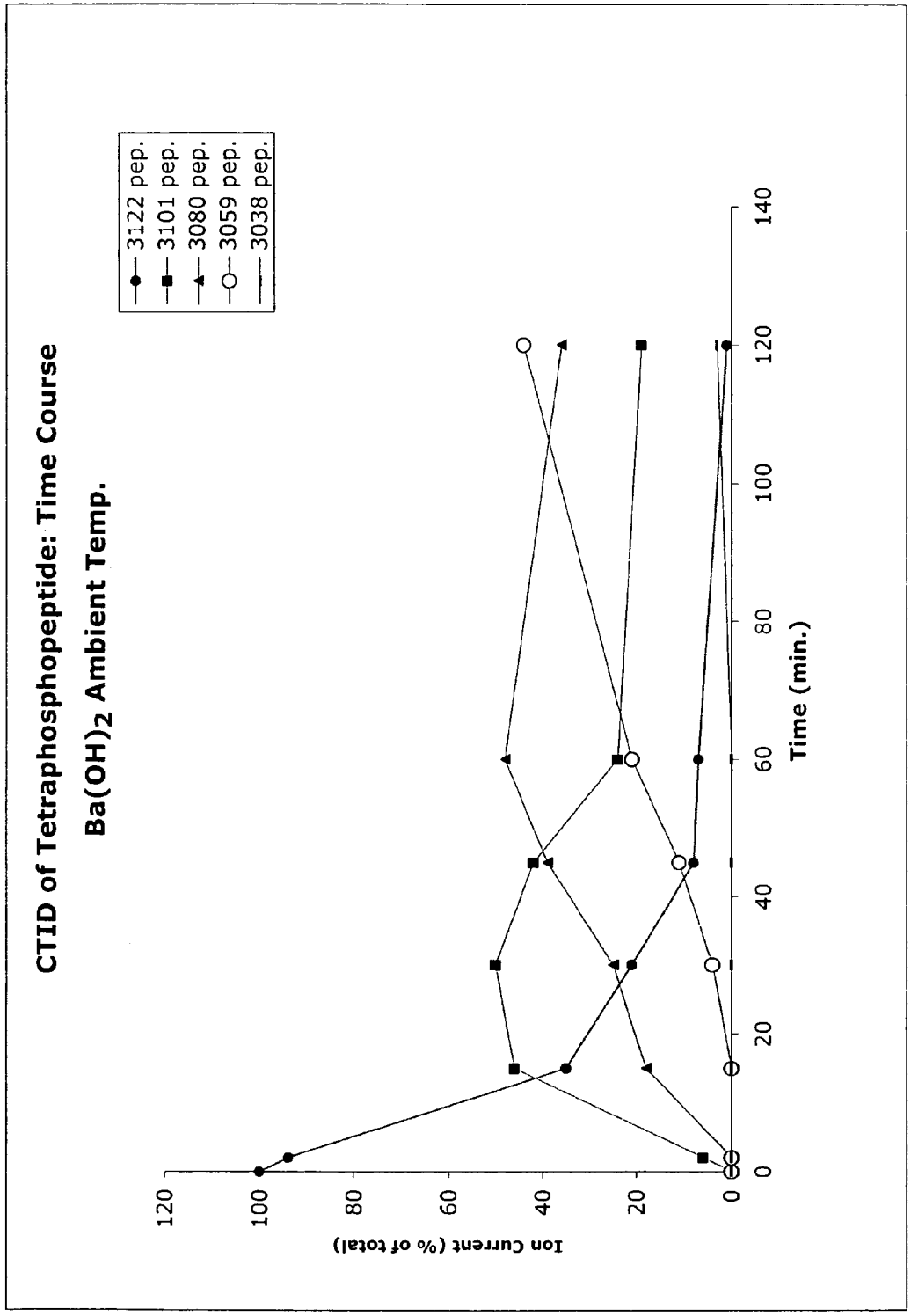
FIG. 4 shows a reaction time course for the chemical conversion of the 3.1 kDa phosphoprotein in a tryptic digest of β-casein (see Table 4). The addition of 2-aminoethanethiol (2-AET) to the phosphorylation sites in the first 25 amino acid residues of β-casein (SEQ ID NO:15) was followed by the change in mass (−21) of the 3.1 kDa tryptic peptide. "Peak height ratio" was determined as the ratio of the ion peak to an unrelated peptide the digest mixture. Closed circles—3122 peptide (SEQ ID NO:16); closed squares—3101 peptide (SEQ ID NO:17); closed triangles, 3080 peptide (SEQ ID NO:18); open circles, 3059 peptide (SEQ ID NO:19), dashes, 3038 peptide (SEQ ID NO:20).

FIG. 4 shows a time course for the conversion of a multiply phosphorylated 3.12 kDa tetra-phosphopeptide from a tryptic digest of bovine β-casein incubated in barium hydroxide in the presence of 2-AET at room temperature. The mass of the anticipated product ions are given in Table 4 and as their m/z values in the inset to FIG. 4. The time course was followed by terminating the reaction at various times, diluting 1:250 and analyzing the products by MALDI-TOF mass spectrometry. The samples were analyzed in triplicate, averaged, and expressed as peak height ratios. The starting peptide ion signal fell over the course of the experiment while the intermediate products were observed to subsequently rise and fall.

TABLE 4

SEQUENCE AND ACCURATE MASS FOR β-CASEIN TRYPTIC PHOSPHOPEPTIDES AND THEIR AMINOETHYLCYSTEINE DERIVATIVES

RELEELNVPGEIVEpSLpSpSpSEESITRINKKIRKFQpSEEQQQTEDE
LQDKIHPFAQTQSLVYPFPGPIPNSLPQNIPPTTPVVVPPFLQPEVMG
VSKVKEAMAPKHKEMPFPKYPVEPFTESQSLTLTDVENLHLPLPLL
QSWMHQPHQPLPPTVMPFPPQSVLSLSQSKVLPVPQKAVPYPQRD
MPIQAFLLYQEPVLGPVRGPFPIIV (15**)

| Peptide Sequence | Mass (calculated) | (observed) |
|---|---|---|
| RELEELNVPGEIVEpS*LpSpSpSEESITR (16) | 3121.3 | 3121.2 |
| RELEELNVPGEIVEpSLpSpSXEESITR (17) | 3100.3 | 3100.3 |
| RELEELNVPGEIVEpSLpSXXEESITR (18) | 3079.4 | 3079.6 |
| RELEELNVPGEIVEpSLXXXEESITR (19) | 3058.4 | 3058.7 |
| RELEELNVPGEIVEXLXXXEESITR (20) | 3037.5 | 3037.7 |
| FQpSEEQQQTEDELQDK (21) | 2060.8 | 2060.8 |
| FQXEEQQQTEDELQDK (22) | 2039.8 | 2040.1 |

Mass analysis was by MALDI-TOF with DHB.
*pS = phosphoserine; X = S-2-aminoethylcysteine
**number in parentheses is SEQ ID NO:.

Table 5 shows the calculated masses of modified peptides cleaved by lysyl endopeptidase. Following chemical modification and lysyl endopeptidase cleavage, the samples were examined by mass analysis. All five serines known to be phosphorylated residues in bovine β-casein were detected. Although the reactions showed a high level of completion, quantitative conversion was not necessary to obtain a valuable read-out. Ions were recorded at 734.4, 1772.0, 2052.1, 2198.1, 2219.1, 2344.2, and 2365.2. These values were in good experimental agreement with the calculated singly charged ions for cleavage on the C-terminal side of serine residues 15, 17, 18, and 19 (see Table 5). At least one peptide was found to contain dehydroalanine, which would result from β-eliminating phosphate without addition of 2-AET.

TABLE 5

MASS ANALYSIS OF CTID ™ PRODUCTS OF β-CASEIN PHOSPHOPEPTIDES

| | (M + H) | | (residues) |
|---|---|---|---|
| | (calc) | (obs) | |
| Tetraphosphopeptide residues 1-25 | | | |
| RELEELNVPGEIVEpS*LpSpSpSEESITR (16**) | 3122.27 | 3122.3 | |
| RELEELNVPGEIVEXLXpSpS (23) | 2365.12 | 2365.2 | 15, 17, 18, 19 |
| RELEELNVPGEIVEXLXpSX (24) | 2344.12 | 2344.2 | 15, 17, 18, 19 |
| RELEELNVPGEIVEXLpSpS (25) | 2219.08 | 2219.1 | 15, 17, 18 |
| RELEELNVPGEIVEXLXpS (26) | 2198.08 | 2198.1 | 15, 17, 18 |
| RELEELNVPGEIVEpSLX (27) | 2051.97 | 2052.1 | 15, 17 |
| RELEELNVPGEIVEX (28) | 1771.88 | 1772.0 | 15 |
| EESITR (29) | 734.37 | 734.4 | 19 |

TABLE 5-continued

MASS ANALYSIS OF CTID ™ PRODUCTS OF β-CASEIN PHOSPHOPEPTIDES

| | (M + H) | | (resi- |
|---|---|---|---|
| | (calc) | (obs) | dues) |
| Phosphopeptide residues 33-48 | | | |
| FQpSEEQQQTEDELQDK (21) | 2061.82 | 2062.1 | |
| FQXEEQQQTEDELQDK (22) | 2057.1 | 2057.2 | |
| EEQQQTEDELQDK (30) | 1619.70 | 1619.7 | 35 |

Tryptic phosphopeptides were converted to their 2-aminoethylcysteine analogs for 2 hr at 25° C.. The mixed reaction products were desalted and digested with lysine endopeptidase overnight at room temperature in 20 mM Tris/HCl, pH 9.2. Mass analysis was by MALDI-TOF with DHB.
*pS = phosphoserine, X = 5-2-aminoethylcysteine
**number in parentheses is SEQ ID NO:.

Figure 5:
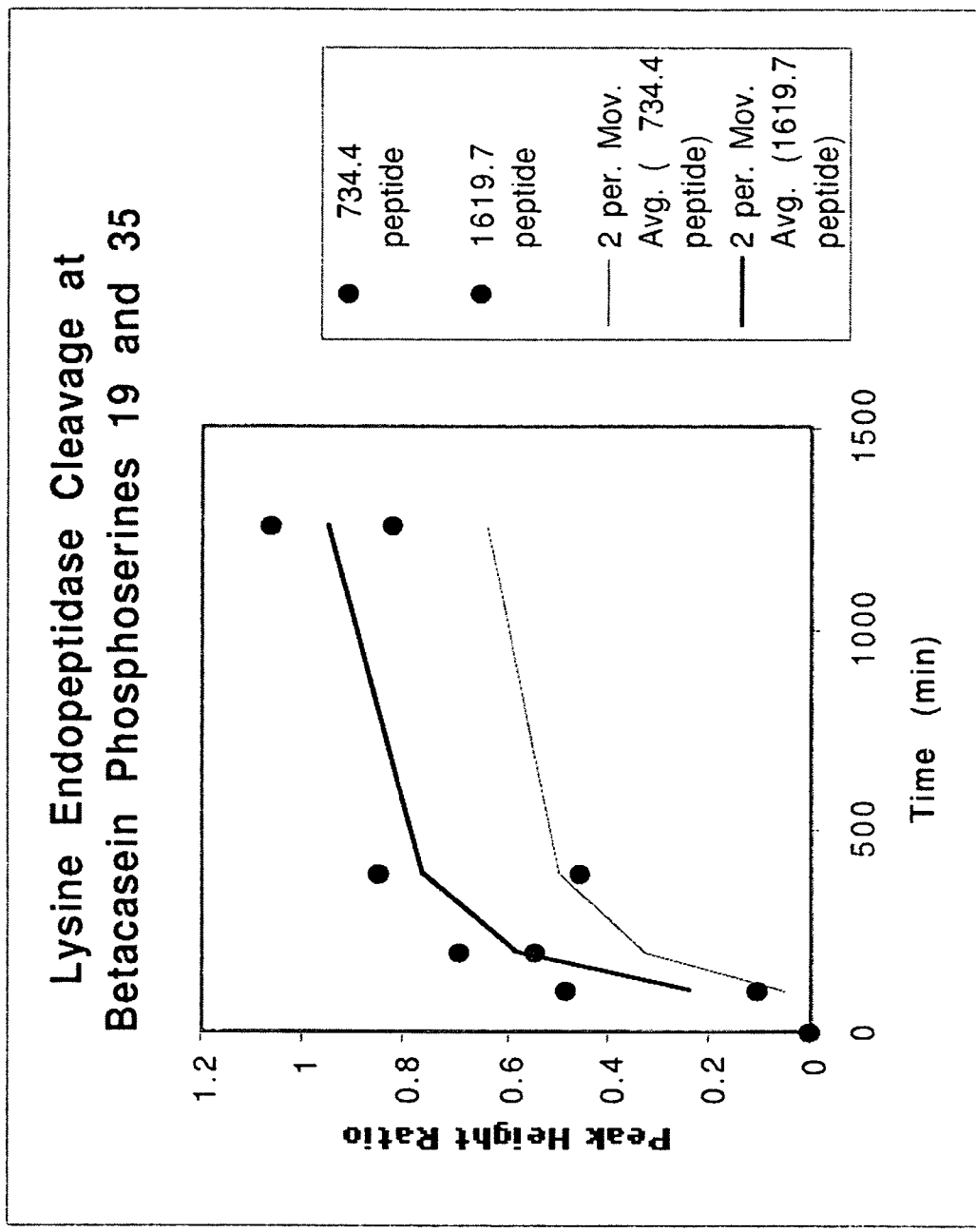
FIG. 5 shows a reaction time course for the cleavage of the 3.1 kDa tryptic fragment of β-casein by lysyl endopeptidase. The phosphopeptide was modified with 2-AET and digested (see Example 2; see, also, Table 5). The fragment from amino acid residues 20-25 (734.4; SEQ ID NO:29) and 36-48 (1619.7; SEQ ID NO:30) were expressed as Peak height ratio (see FIG. 4, above).

FIG. 5 shows a time course of enzymatic cleavage of two modified phosphopeptides. A 2.06 kDa phosphopeptide and a 3.12 kDa tetra-phosphopeptide from a tryptic digest of β-casein were modified by the CTID™ method and subjected to proteolysis by lysine endopeptidase at pH 9.2 in Tris/HCl buffer. The anticipated C-terminal fragment EEQQQT-EDELQDK (SEQ ID NO:36) calc. m/z 1619.7 from the singly-phosphorylated peptide (residues 32-48 of β-casein) and the C-terminal fragment EESITR (SEQ ID NO:29) calc. m/z 734.4 from the tetra-phosphopeptide (residues 1-25 of β-casein) were followed.

These results demonstrate that chemically target identification of phosphorylated amino acid residues can be performed using proteolytic digests of phosphoproteins.

Although the invention has been described with reference to the above example, it will be understood that modifications and variations are encompassed within the spirit and scope of the invention. Accordingly, the invention is limited only by the following claims.

What is claimed is:

1. A method for identifying a position of at least one post-translationally modified (PTM) amino acid residue in at least one peptide, comprising
   a) treating a sample comprising at least one peptide with at least one reagent that can chemically modify a PTM amino acid residue of a peptide, wherein the PTM amino acid residue comprises a phosphorylated amino acid residue, whereby, when a peptide comprises at least one PTM amino acid residue, a peptide comprising at least one chemically modified amino acid residue is generated,
   wherein the peptide is susceptible to cleavage by a proteolytic agent at the position of the chemically modified amino acid residue, and
   wherein the peptide is not susceptible to cleavage by the proteolytic agent at the position of the PTM amino acid residue prior to chemically modifying the PTM amino acid residue;
   b) contacting the peptide comprising the chemically modified amino acid residue with the proteolytic agent, whereby the peptide is cleaved at the position of the chemically modified amino acid residue to produce cleavage products indicative of the position of a PTM amino acid residue in the peptide; and
   c) determining the mass of one or more of the cleaved products, thereby identifying the position of at least one PTM amino acid residue in at least one peptide.

2. The method of claim 1, wherein the PTM amino acid residue comprises a phosphoserine residue or a phosphothreonine residue.

3. The method of claim 2, wherein the sample is treated with a first reagent comprising a base that effects β-elimination of the PTM amino acid residue of the peptide to generate an alanine derivative, and a second reagent comprising a nucleophile that effects Michael addition of the alanine derivative, thereby generating a chemically modified amino acid residue comprising a lysine analog.

4. The method of claim 1, wherein the proteolytic agent comprises an enzyme.

5. The method of claim 3, wherein the proteolytic agent comprises an endopeptidase that cleaves a peptide at a lysine residue or a lysine analog.

6. The method of claim 5, wherein the endopeptidase is *Achromobacter lyticus* lysyl endopeptidase or *Lysobacter enzymogenes* endoprotease Lys-C.

7. The method of claim 1, further comprising blocking at least one substrate amino acid residue in the peptide, wherein the substrate amino acid residue is not the PTM amino acid residue to be chemically modified.

8. The method of claim 1, comprising measuring the mass of at least one cleavage product, wherein the mass is indicative of the position of the PTM amino acid residue.

9. The method of claim 8, wherein the mass of a cleavage product is determined by mass spectrometry.

10. The method of claim 1, further comprising determining the identity of at least one PTM amino acid residue.

11. The method of claim 1, further comprising determining whether a PTM amino acid residue comprises a phosphoamino acid residue, comprising, prior to chemically modifying the PTM amino acid residue,
   contacting an aliquot of the sample comprising the peptide with a glycosidase,
   thereafter treating the aliquot of the sample with a reagent that can chemically modify the PTM amino acid residue, when present, and contacting the peptide of the aliquot with the proteolytic agent,
   wherein cleavage of the peptide of the aliquot corresponding to cleavage of the peptide comprising the chemically modified amino acid residue is indicative of the PTM amino acid residue comprising a phosphoamino acid residue.

12. The method of claim 1, wherein the sample comprises a plurality of peptides.

13. The method of claim 12, wherein the plurality of peptides comprises at least two different peptides, each of which comprises at least one PTM amino acid residue.

14. The method of claim 12, wherein the plurality of peptides comprises peptide fragments of a protein.

15. The method of claim 12, which comprises a multiplex analysis.

16. The method of claim 1, which is performed in a high throughput format.

17. A method for identifying a position of at least one post-translationally modified (PTM) amino acid residue in at least one peptide, wherein the PTM amino acid residue comprises phosphoserine, or phosphothreonine, comprising
    a) chemically modifying the PTM amino acid residue of at least one peptide of a sample to produce a lysine analog, thereby generating a peptide comprising at least one lysine analog;
    b) contacting the peptide comprising the lysine analog with a lysine specific proteolytic agent, whereby the peptide is cleaved at the position of the lysine analog to produce cleavage products indicative of the position of a PTM amino acid residue in the peptide; and
    c) determining the mass of one or more of the cleaved products, thereby identifying the position of at least one PTM amino acid residue in at least one peptide.

18. The method of claim 17, wherein the lysine specific proteolytic agent comprises an enzyme.

19. The method of claim 17, wherein the peptide comprising the PTM amino acid residue is coupled to a solid support.

20. The method of claim 19, wherein the solid support comprises a bead, a glass slide, a well, or a chip.

21. The method of claim 17, wherein chemically modifying the PTM amino acid residue of the peptide comprises contacting the PTM amino acid residue with
    a first reagent comprising a base that effects β-elimination of the PTM amino acid residue to generate an alanine derivative by β-elimination, and
    a second reagent comprising a nucleophile that effects Michael addition of the alanine derivative.

22. The method of claim 17, wherein the peptide comprises a plurality of peptides.

23. A kit, comprising:
    a) a reagent that effects β-elimination of a phosphoserine, or phosphothreonine, residue of a peptide to produce an amino acid analog Michael acceptor;
    b) a reagent comprising a nucleophile that can interact with the amino acid Michael acceptor to produce a chemically modified amino acid residue in a peptide;
    c) one or more proteolytic agents that can cleave a peptide at the position of the chemically modified amino acid residue formed by β-elimination and Michael addition of phosphoserine, or phosphothreonine residue; and
    d) at least one container comprising the reagents and agents.

24. The kit of claim 23, wherein
the reagent that effects β-elimination comprises sodium hydroxide, barium hydroxide, ammonium hydroxide, or a combination thereof;
the nucleophile comprises an amine, a thiol, or a combination thereof; and
the one or more proteolytic agents comprise at least one enzyme.

25. The kit of claim 24, wherein the nucleophile comprises 2-aminoethanethiol, 1,2-diaminoethane, or a combination thereof.

26. The kit of claim 24, wherein the at least one enzyme is lysyl endopeptidase, endoprotease Lys-C, or a combination thereof.

27. The kit of claim 23, further comprising a peptide comprising at least one phosphoamino acid residue.

* * * * *

SEQUENCE LISTING

```
<160> NUMBER OF SEQ ID NOS: 35

<210> SEQ ID NO 1
<211> LENGTH: 7
<212> TYPE: PRT
<213> ORGANISM: Artificial sequence
<220> FEATURE:
<223> OTHER INFORMATION: Synthetic construct: Post-translationally
      modified peptide
<220> FEATURE:
<221> NAME/KEY: MISC_FEATURE
<222> LOCATION: (5)..(5)
<223> OTHER INFORMATION: Xaa is phosphothreonine

<400> SEQUENCE: 1

Leu Lys Arg Ala Xaa Leu Gly
1               5

<210> SEQ ID NO 2
<211> LENGTH: 11
<212> TYPE: PRT
<213> ORGANISM: Artificial sequence
<220> FEATURE:
<223> OTHER INFORMATION: Synthetic construct: Post-translationally
      modified peptide
<220> FEATURE:
<221> NAME/KEY: MISC_FEATURE
<222> LOCATION: (4)..(4)
<223> OTHER INFORMATION: Xaa is phosphoserine

<400> SEQUENCE: 2

Lys Arg Pro Xaa Gln Arg His Gly Ser Lys Tyr
1               5                   10

<210> SEQ ID NO 3
<211> LENGTH: 19
<212> TYPE: PRT
<213> ORGANISM: Artificial sequence
<220> FEATURE:
<223> OTHER INFORMATION: Synthetic construct: Post-translationally
      modified peptide
<220> FEATURE:
<221> NAME/KEY: MISC_FEATURE
<222> LOCATION: (15)..(15)
<223> OTHER INFORMATION: Xaa is phosphoserine

<400> SEQUENCE: 3
```

```
Asp Leu Asp Val Pro Ile Pro Gly Arg Phe Asp Arg Arg Val Xaa Val
1               5                   10                  15

Ala Ala Glu

<210> SEQ ID NO 4
<211> LENGTH: 9
<212> TYPE: PRT
<213> ORGANISM: Artificial sequence
<220> FEATURE:
<223> OTHER INFORMATION: Synthetic construct: Post-translationally
      modified peptide
<220> FEATURE:
<221> NAME/KEY: MISC_FEATURE
<222> LOCATION: (4)..(4)
<223> OTHER INFORMATION: Xaa is O-GlcNAc-serine

<400> SEQUENCE: 4

Phe Ala Ala Xaa Asn Tyr Pro Ala Leu
1               5

<210> SEQ ID NO 5
<211> LENGTH: 5
<212> TYPE: PRT
<213> ORGANISM: Artificial sequence
<220> FEATURE:
<223> OTHER INFORMATION: Synthetic construct: Peptide cleavage product
<220> FEATURE:
<221> NAME/KEY: MISC_FEATURE
<222> LOCATION: (5)..(5)
<223> OTHER INFORMATION: Xaa is 2-aminoethanethiol modified residue

<400> SEQUENCE: 5

Leu Lys Arg Ala Xaa
1               5

<210> SEQ ID NO 6
<211> LENGTH: 2
<212> TYPE: PRT
<213> ORGANISM: Artificial sequence
<220> FEATURE:
<223> OTHER INFORMATION: Synthetic construct: Peptide cleavage product

<400> SEQUENCE: 6

Leu Gly
1

<210> SEQ ID NO 7
<211> LENGTH: 4
<212> TYPE: PRT
<213> ORGANISM: Artificial sequence
<220> FEATURE:
<223> OTHER INFORMATION: Synthetic construct: Peptide cleavage product
<220> FEATURE:
<221> NAME/KEY: MISC_FEATURE
<222> LOCATION: (4)..(4)
<223> OTHER INFORMATION: Xaa is 2-aminoethanethiol modified residue

<400> SEQUENCE: 7

Lys Arg Pro Xaa
1

<210> SEQ ID NO 8
<211> LENGTH: 7
<212> TYPE: PRT
<213> ORGANISM: Artificial sequence
<220> FEATURE:
<223> OTHER INFORMATION: Synthetic construct: Peptide cleavage product
```

```
<400> SEQUENCE: 8

Gln Arg His Gly Ser Lys Tyr
1               5

<210> SEQ ID NO 9
<211> LENGTH: 14
<212> TYPE: PRT
<213> ORGANISM: Artificial sequence
<220> FEATURE:
<223> OTHER INFORMATION: Synthetic construct: Peptide cleavage product
<220> FEATURE:
<221> NAME/KEY: MISC_FEATURE
<222> LOCATION: (14)..(14)
<223> OTHER INFORMATION: Xaa is 2-aminoethanethiol modified residue

<400> SEQUENCE: 9

Asp Leu Asp Val Pro Ile Pro Gly Arg Phe Asp Arg Arg Xaa
1               5                   10

<210> SEQ ID NO 10
<211> LENGTH: 4
<212> TYPE: PRT
<213> ORGANISM: Artificial sequence
<220> FEATURE:
<223> OTHER INFORMATION: Synthetic construct: Peptide cleavage product

<400> SEQUENCE: 10

Val Ala Ala Glu
1

<210> SEQ ID NO 11
<211> LENGTH: 4
<212> TYPE: PRT
<213> ORGANISM: Artificial sequence
<220> FEATURE:
<223> OTHER INFORMATION: Synthetic construct: Peptide cleavage product
<220> FEATURE:
<221> NAME/KEY: MISC_FEATURE
<222> LOCATION: (4)..(4)
<223> OTHER INFORMATION: Xaa is 2-aminoethanethiol modified residue

<400> SEQUENCE: 11

Phe Ala Ala Xaa
1

<210> SEQ ID NO 12
<211> LENGTH: 5
<212> TYPE: PRT
<213> ORGANISM: Artificial sequence
<220> FEATURE:
<223> OTHER INFORMATION: Synthetic construct: Peptide cleavage product

<400> SEQUENCE: 12

Asn Tyr Pro Ala Leu
1               5

<210> SEQ ID NO 13
<211> LENGTH: 5
<212> TYPE: PRT
<213> ORGANISM: Artificial sequence
<220> FEATURE:
<223> OTHER INFORMATION: Synthetic construct: Fragment of SEQ ID NO:3

<400> SEQUENCE: 13

Asp Leu Asp Val Pro
1               5
```

-continued

```
<210> SEQ ID NO 14
<211> LENGTH: 6
<212> TYPE: PRT
<213> ORGANISM: Artificial sequence
<220> FEATURE:
<223> OTHER INFORMATION: Synthetic construct: Chemically modified
      peptide
<220> FEATURE:
<221> NAME/KEY: MISC_FEATURE
<222> LOCATION: (6)..(6)
<223> OTHER INFORMATION: Xaa is acetylated lysine

<400> SEQUENCE: 14

Gln Arg His Gly Ser Xaa
1               5

<210> SEQ ID NO 15
<211> LENGTH: 208
<212> TYPE: PRT
<213> ORGANISM: Bovine
<220> FEATURE:
<221> NAME/KEY: MISC_FEATURE
<222> LOCATION: (15)..(15)
<223> OTHER INFORMATION: Xaa is phosphoserine
<220> FEATURE:
<221> NAME/KEY: MISC_FEATURE
<222> LOCATION: (17)..(19)
<223> OTHER INFORMATION: Xaa is phosphoserine
<220> FEATURE:
<221> NAME/KEY: MISC_FEATURE
<222> LOCATION: (35)..(35)
<223> OTHER INFORMATION: Xaa is phosphoserine

<400> SEQUENCE: 15

Arg Glu Leu Glu Glu Leu Asn Val Pro Gly Glu Ile Val Glu Xaa Leu
1               5                   10                  15

Xaa Xaa Xaa Glu Glu Ser Ile Thr Arg Ile Asn Lys Lys Ile Glu Lys
                20                  25                  30

Phe Gln Xaa Glu Glu Gln Gln Gln Thr Glu Asp Glu Leu Gln Asp Lys
                35                  40                  45

Ile His Pro Phe Ala Gln Thr Gln Ser Leu Val Tyr Pro Phe Pro Gly
        50                  55                  60

Pro Ile Pro Asn Ser Leu Pro Gln Asn Ile Pro Pro Leu Thr Thr Pro
65                  70                  75                  80

Val Val Val Pro Pro Phe Leu Gln Pro Glu Val Met Gly Val Ser Lys
                85                  90                  95

Val Lys Glu Ala Met Ala Pro Lys His Lys Glu Met Pro Phe Pro Lys
                100                 105                 110

Tyr Pro Val Glu Pro Phe Thr Glu Ser Gln Ser Leu Thr Leu Thr Asp
            115                 120                 125

Val Glu Asn Leu His Leu Pro Leu Pro Leu Leu Gln Ser Trp Met His
    130                 135                 140

Gln Pro His Gln Pro Leu Pro Pro Thr Val Met Phe Pro Pro Gln Ser
145                 150                 155                 160

Val Leu Ser Leu Ser Gln Ser Lys Val Leu Pro Val Pro Gln Lys Ala
                165                 170                 175

Val Pro Tyr Pro Gln Arg Asp Met Pro Ile Gln Ala Phe Leu Leu Tyr
            180                 185                 190

Gln Glu Pro Val Leu Gly Pro Val Arg Gly Pro Phe Pro Ile Ile Val
        195                 200                 205

<210> SEQ ID NO 16
<211> LENGTH: 25
```

```
<212> TYPE: PRT
<213> ORGANISM: Artificial sequence
<220> FEATURE:
<223> OTHER INFORMATION: Bovine: Fragment of SEQ ID NO:15
<220> FEATURE:
<221> NAME/KEY: MISC_FEATURE
<222> LOCATION: (15)..(15)
<223> OTHER INFORMATION: Xaa is phosphoserine
<220> FEATURE:
<221> NAME/KEY: MISC_FEATURE
<222> LOCATION: (17)..(19)
<223> OTHER INFORMATION: Xaa is phosphoserine

<400> SEQUENCE: 16

Arg Glu Leu Glu Glu Leu Asn Val Pro Gly Glu Ile Val Glu Xaa Leu
1               5                   10                  15

Xaa Xaa Xaa Glu Glu Ser Ile Thr Arg
            20                  25

<210> SEQ ID NO 17
<211> LENGTH: 25
<212> TYPE: PRT
<213> ORGANISM: Artificial sequence
<220> FEATURE:
<223> OTHER INFORMATION: Synthetic construct: Peptide cleavage product
<220> FEATURE:
<221> NAME/KEY: MISC_FEATURE
<222> LOCATION: (15)..(15)
<223> OTHER INFORMATION: Xaa is phosphoserine
<220> FEATURE:
<221> NAME/KEY: MISC_FEATURE
<222> LOCATION: (17)..(18)
<223> OTHER INFORMATION: Xaa is phosphoserine
<220> FEATURE:
<221> NAME/KEY: MISC_FEATURE
<222> LOCATION: (19)..(19)
<223> OTHER INFORMATION: Xaa is S-2-aminoethylcysteine

<400> SEQUENCE: 17

Arg Glu Leu Glu Glu Leu Asn Val Pro Gly Glu Ile Val Glu Xaa Leu
1               5                   10                  15

Xaa Xaa Xaa Glu Glu Ser Ile Thr Arg
            20                  25

<210> SEQ ID NO 18
<211> LENGTH: 25
<212> TYPE: PRT
<213> ORGANISM: Artificial sequence
<220> FEATURE:
<223> OTHER INFORMATION: Synthetic construct: Peptide cleavage product
<220> FEATURE:
<221> NAME/KEY: MISC_FEATURE
<222> LOCATION: (15)..(15)
<223> OTHER INFORMATION: Xaa is phosphoserine
<220> FEATURE:
<221> NAME/KEY: MISC_FEATURE
<222> LOCATION: (17)..(17)
<223> OTHER INFORMATION: Xaa is phosphoserine
<220> FEATURE:
<221> NAME/KEY: MISC_FEATURE
<222> LOCATION: (18)..(19)
<223> OTHER INFORMATION: Xaa is S-2-aminoethylcysteine

<400> SEQUENCE: 18

Arg Glu Leu Glu Glu Leu Asn Val Pro Gly Glu Ile Val Glu Xaa Leu
1               5                   10                  15

Xaa Xaa Xaa Glu Glu Ser Ile Thr Arg
            20                  25

<210> SEQ ID NO 19
```

```
<211> LENGTH: 25
<212> TYPE: PRT
<213> ORGANISM: Artificial sequence
<220> FEATURE:
<223> OTHER INFORMATION: Synthetic construct: Peptide cleavage product
<220> FEATURE:
<221> NAME/KEY: MISC_FEATURE
<222> LOCATION: (15)..(15)
<223> OTHER INFORMATION: Xaa is phosphoserine
<220> FEATURE:
<221> NAME/KEY: MISC_FEATURE
<222> LOCATION: (17)..(19)
<223> OTHER INFORMATION: Xaa is S-2-aminoethylcysteine

<400> SEQUENCE: 19

Arg Glu Leu Glu Glu Leu Asn Val Pro Gly Glu Ile Val Glu Xaa Leu
1               5                   10                  15

Xaa Xaa Xaa Glu Glu Ser Ile Thr Arg
            20                  25

<210> SEQ ID NO 20
<211> LENGTH: 25
<212> TYPE: PRT
<213> ORGANISM: Artificial sequence
<220> FEATURE:
<223> OTHER INFORMATION: Synthetic construct: Peptide cleavage product
<220> FEATURE:
<221> NAME/KEY: MISC_FEATURE
<222> LOCATION: (15)..(19)
<223> OTHER INFORMATION: Xaa is S-2-aminoethylcysteine

<400> SEQUENCE: 20

Arg Glu Leu Glu Glu Leu Asn Val Pro Gly Glu Ile Val Glu Xaa Leu
1               5                   10                  15

Xaa Xaa Xaa Glu Glu Ser Ile Thr Arg
            20                  25

<210> SEQ ID NO 21
<211> LENGTH: 16
<212> TYPE: PRT
<213> ORGANISM: Artificial sequence
<220> FEATURE:
<223> OTHER INFORMATION: Synthetic construct: Peptide cleavage product
<220> FEATURE:
<221> NAME/KEY: MISC_FEATURE
<222> LOCATION: (3)..(3)
<223> OTHER INFORMATION: Xaa is phosphoserine

<400> SEQUENCE: 21

Phe Gln Xaa Glu Glu Gln Gln Gln Thr Glu Asp Glu Leu Gln Asp Lys
1               5                   10                  15

<210> SEQ ID NO 22
<211> LENGTH: 16
<212> TYPE: PRT
<213> ORGANISM: Artificial sequence
<220> FEATURE:
<223> OTHER INFORMATION: Synthetic construct: Peptide cleavage product
<220> FEATURE:
<221> NAME/KEY: MISC_FEATURE
<222> LOCATION: (3)..(3)
<223> OTHER INFORMATION: Xaa is S-2-aminoethylcysteine

<400> SEQUENCE: 22

Phe Gln Xaa Glu Glu Gln Gln Gln Thr Glu Asp Glu Leu Gln Asp Lys
1               5                   10                  15

<210> SEQ ID NO 23
<211> LENGTH: 19
```

```
<212> TYPE: PRT
<213> ORGANISM: Artificial sequence
<220> FEATURE:
<223> OTHER INFORMATION: Synthetic construct: Peptide cleavage product
<220> FEATURE:
<221> NAME/KEY: MISC_FEATURE
<222> LOCATION: (15)..(15)
<223> OTHER INFORMATION: Xaa is S-2-aminoethylcysteine
<220> FEATURE:
<221> NAME/KEY: MISC_FEATURE
<222> LOCATION: (17)..(17)
<223> OTHER INFORMATION: Xaa is S-2-aminoethylcysteine
<220> FEATURE:
<221> NAME/KEY: MISC_FEATURE
<222> LOCATION: (18)..(19)
<223> OTHER INFORMATION: Xaa is phosphoserine

<400> SEQUENCE: 23

Arg Glu Leu Glu Glu Leu Asn Val Pro Gly Glu Ile Val Glu Xaa Leu
1               5                   10                  15

Xaa Xaa Xaa

<210> SEQ ID NO 24
<211> LENGTH: 19
<212> TYPE: PRT
<213> ORGANISM: Artificial sequence
<220> FEATURE:
<223> OTHER INFORMATION: Synthetic construct: Peptide cleavage product
<220> FEATURE:
<221> NAME/KEY: MISC_FEATURE
<222> LOCATION: (15)..(15)
<223> OTHER INFORMATION: Xaa is S-2-aminoethylcysteine
<220> FEATURE:
<221> NAME/KEY: MISC_FEATURE
<222> LOCATION: (17)..(17)
<223> OTHER INFORMATION: Xaa is S-2-aminoethylcysteine
<220> FEATURE:
<221> NAME/KEY: MISC_FEATURE
<222> LOCATION: (18)..(18)
<223> OTHER INFORMATION: Xaa is phosphoserine
<220> FEATURE:
<221> NAME/KEY: MISC_FEATURE
<222> LOCATION: (19)..(19)
<223> OTHER INFORMATION: Xaa is S-2-aminoethylcysteine

<400> SEQUENCE: 24

Arg Glu Leu Glu Glu Leu Asn Val Pro Gly Glu Ile Val Glu Xaa Leu
1               5                   10                  15

Xaa Xaa Xaa

<210> SEQ ID NO 25
<211> LENGTH: 18
<212> TYPE: PRT
<213> ORGANISM: Artificial sequence
<220> FEATURE:
<223> OTHER INFORMATION: Synthetic construct: Peptide cleavage product
<220> FEATURE:
<221> NAME/KEY: MISC_FEATURE
<222> LOCATION: (15)..(15)
<223> OTHER INFORMATION: Xaa is S-2-aminoethylcysteine
<220> FEATURE:
<221> NAME/KEY: MISC_FEATURE
<222> LOCATION: (17)..(18)
<223> OTHER INFORMATION: Xaa is phosphoserine

<400> SEQUENCE: 25

Arg Glu Leu Glu Glu Leu Asn Val Pro Gly Glu Ile Val Glu Xaa Leu
1               5                   10                  15

Xaa Xaa
```

```
<210> SEQ ID NO 26
<211> LENGTH: 18
<212> TYPE: PRT
<213> ORGANISM: Artificial sequence
<220> FEATURE:
<223> OTHER INFORMATION: Synthetic construct: Peptide cleavage product
<220> FEATURE:
<221> NAME/KEY: MISC_FEATURE
<222> LOCATION: (15)..(15)
<223> OTHER INFORMATION: Xaa is S-2-aminoethylcysteine
<220> FEATURE:
<221> NAME/KEY: MISC_FEATURE
<222> LOCATION: (17)..(17)
<223> OTHER INFORMATION: Xaa is S-2-aminoethylcysteine
<220> FEATURE:
<221> NAME/KEY: MISC_FEATURE
<222> LOCATION: (18)..(18)
<223> OTHER INFORMATION: Xaa is phosphoserine

<400> SEQUENCE: 26

Arg Glu Leu Glu Glu Leu Asn Val Pro Gly Glu Ile Val Glu Xaa Leu
1               5                   10                  15

Xaa Xaa

<210> SEQ ID NO 27
<211> LENGTH: 17
<212> TYPE: PRT
<213> ORGANISM: Artificial sequence
<220> FEATURE:
<223> OTHER INFORMATION: Synthetic construct: Peptide cleavage product
<220> FEATURE:
<221> NAME/KEY: MISC_FEATURE
<222> LOCATION: (15)..(15)
<223> OTHER INFORMATION: Xaa is phosphoserine
<220> FEATURE:
<221> NAME/KEY: MISC_FEATURE
<222> LOCATION: (17)..(17)
<223> OTHER INFORMATION: Xaa is S-2-aminoethylcysteine

<400> SEQUENCE: 27

Arg Glu Leu Glu Glu Leu Asn Val Pro Gly Glu Ile Val Glu Xaa Leu
1               5                   10                  15

Xaa

<210> SEQ ID NO 28
<211> LENGTH: 15
<212> TYPE: PRT
<213> ORGANISM: Artificial sequence
<220> FEATURE:
<223> OTHER INFORMATION: Synthetic construct: Peptide cleavage product
<220> FEATURE:
<221> NAME/KEY: MISC_FEATURE
<222> LOCATION: (15)..(15)
<223> OTHER INFORMATION: Xaa is S-2-aminoethylcysteine

<400> SEQUENCE: 28

Arg Glu Leu Glu Glu Leu Asn Val Pro Gly Glu Ile Val Glu Xaa
1               5                   10                  15

<210> SEQ ID NO 29
<211> LENGTH: 6
<212> TYPE: PRT
<213> ORGANISM: Artificial sequence
<220> FEATURE:
<223> OTHER INFORMATION: Bovine: Fragment of SEQ ID NO:15

<400> SEQUENCE: 29

Glu Glu Ser Ile Thr Arg
1               5
```

<210> SEQ ID NO 30
<211> LENGTH: 13
<212> TYPE: PRT
<213> ORGANISM: Artificial sequence
<220> FEATURE:
<223> OTHER INFORMATION: Bovine: Fragment of SEQ ID NO:15

<400> SEQUENCE: 30

Glu Glu Gln Gln Gln Thr Glu Asp Glu Leu Gln Asp Lys
1               5                   10

<210> SEQ ID NO 31
<211> LENGTH: 4
<212> TYPE: PRT
<213> ORGANISM: Artificial sequence
<220> FEATURE:
<223> OTHER INFORMATION: Synthetic construct: Peptide containing a
      C-terminal motif
<220> FEATURE:
<221> NAME/KEY: MISC_FEATURE
<222> LOCATION: (4)..(4)
<223> OTHER INFORMATION: Xaa is any amino acid

<400> SEQUENCE: 31

Cys Ala Ala Xaa
1

<210> SEQ ID NO 32
<211> LENGTH: 9
<212> TYPE: PRT
<213> ORGANISM: Artificial sequence
<220> FEATURE:
<223> OTHER INFORMATION: Synthetic construct: Peptide cleavage product
<220> FEATURE:
<221> NAME/KEY: MISC_FEATURE
<222> LOCATION: (6)..(6)
<223> OTHER INFORMATION: Xaa is 2-aminoethanethiol modified peptide
<220> FEATURE:
<221> NAME/KEY: MISC_FEATURE
<222> LOCATION: (7)..(7)
<223> OTHER INFORMATION: Xaa is Val or Ala

<400> SEQUENCE: 32

Phe Asp Arg Arg Val Xaa Xaa Ala Glu
1               5

<210> SEQ ID NO 33
<211> LENGTH: 3
<212> TYPE: PRT
<213> ORGANISM: Artificial sequence
<220> FEATURE:
<223> OTHER INFORMATION: Synthetic construct: Peptide cleavage product

<400> SEQUENCE: 33

Val Ala Ala
1

<210> SEQ ID NO 34
<211> LENGTH: 3
<212> TYPE: PRT
<213> ORGANISM: Artificial sequence
<220> FEATURE:
<223> OTHER INFORMATION: Synthetic construct: Chemically modified
      peptide
<220> FEATURE:
<221> NAME/KEY: MISC_FEATURE
<222> LOCATION: (1)..(1)
<223> OTHER INFORMATION: Xaa is acetylated leucine
<220> FEATURE:
<221> NAME/KEY: MISC_FEATURE -continued

```
<222> LOCATION: (2)..(2)
<223> OTHER INFORMATION: Xaa is acetylated lysine

<400> SEQUENCE: 34

Xaa Xaa Arg
1

<210> SEQ ID NO 35
<211> LENGTH: 5
<212> TYPE: PRT
<213> ORGANISM: Artificial sequence
<220> FEATURE:
<223> OTHER INFORMATION: Synthetic construct: Chemically modified
      peptide
<220> FEATURE:
<221> NAME/KEY: MISC_FEATURE
<222> LOCATION: (1)..(1)
<223> OTHER INFORMATION: Xaa is acetylated leucine
<220> FEATURE:
<221> NAME/KEY: MISC_FEATURE
<222> LOCATION: (2)..(2)
<223> OTHER INFORMATION: Xaa is acetylated lysine
<220> FEATURE:
<221> NAME/KEY: MISC_FEATURE
<222> LOCATION: (5)..(5)
<223> OTHER INFORMATION: Xaa is 2-aminoethamethiol modified residue

<400> SEQUENCE: 35

Xaa Xaa Arg Ala Xaa
1               5
```